US012193850B2

United States Patent
Deng et al.

(10) Patent No.: US 12,193,850 B2
(45) Date of Patent: Jan. 14, 2025

(54) MULTI-USER SURGICAL CART

(71) Applicant: NuVasive, Inc., San Diego, CA (US)

(72) Inventors: Brian Deng, Encinitas, CA (US); Chris Ryan, San Diego, CA (US); Dmitry Novikov, San Diego, CA (US); Natallia Ivaniuk, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 291 days.

(21) Appl. No.: 17/688,574

(22) Filed: Mar. 7, 2022

(65) Prior Publication Data

US 2022/0296326 A1  Sep. 22, 2022

Related U.S. Application Data

(60) Provisional application No. 63/164,442, filed on Mar. 22, 2021.

(51) Int. Cl.
*G16H 40/67* (2018.01)
*A61B 50/13* (2016.01)
*A61B 90/00* (2016.01)

(52) U.S. Cl.
CPC ............ *A61B 50/13* (2016.02); *A61B 90/361* (2016.02); *G16H 40/67* (2018.01)

(58) Field of Classification Search
CPC ....... A61B 50/13; A61B 90/361; G16H 40/67
See application file for complete search history.

(56) References Cited

U.S. PATENT DOCUMENTS

| 2010/0082372 | A1* | 4/2010 | Wen | G06Q 10/06 705/2 |
| 2013/0018666 | A1* | 1/2013 | Murphy | A61B 17/58 705/2 |
| 2013/0305341 | A1* | 11/2013 | Baker | H04W 28/26 726/11 |
| 2017/0065361 | A1* | 3/2017 | Kurita | A61B 5/026 |
| 2018/0092699 | A1 | 4/2018 | Finley | |
| 2021/0196406 | A1* | 7/2021 | Mahadik | G06F 21/6218 |
| 2022/0192770 | A1* | 6/2022 | White | A61B 90/98 |

OTHER PUBLICATIONS

Villarreal, M. C., & Keskinocak, P. (2016). Staff planning for operating rooms with different surgical services lines. Health Care Management Science (Year: 2016).*
International Search Report and Written Opinion dated May 24, 2022 for International Application No. PCT/US2022/019190.
"How to connect to the EVC Wireless Network using a Windows 10 computer", ITSS Help Desk, 3 Pages, Revised Oct. 16, 2020, https://services.sjeccd.edu/TDClient/1862/Portal/Shared/FileOpen?AttachmentID=01bdb6f7-8cfa-445d-84b5-2746c5f304de&ItemID=118604&ItemComponent=26&IsInline=-1, Retrieved May 6, 2022.
"Multi-Factor Authentication", Wikipedia, Revised Apr. 13, 2018, https://en.wikipedia.org/w/index.php?title=Multi-factor_authentication&oldid=836192629, Retrieved Feb. 18, 2022.

* cited by examiner

*Primary Examiner* — Matthew L Hamilton

(57) ABSTRACT

A system includes a surgical cart that includes a local client access point, a monitor, a cart computer, a first external interface coupled to the local client access point, and a second external interface coupled to the primary monitor. The surgical cart can host a web server to which one or more client devices can connect using a web browser. The web server can provide access to one or more surgical applications hosted by the surgical cart during a surgery.

18 Claims, 9 Drawing Sheets

MULTI-USER SURGICAL CART

CROSS-REFERENCE TO RELATED APPLICATIONS

This application claims priority to U.S. Provisional Patent Application 63/164,442, which was filed Mar. 22, 2021, and which is incorporated herein by reference in its entirety for any and all purposes.

BACKGROUND

In surgical procedures, such as spinal fusion, surgeons and other healthcare professionals make tradeoffs between invasiveness, efficiency, and radiation exposure to accomplish surgical objectives. Various technologies have been introduced into the operating room in order to help navigate these and other tradeoffs, but often result in proliferation of stand-alone technology, which can create challenges in a constrained operating room footprint.

SUMMARY

In an example, there is a method performed during a surgery or in preparation for a surgery in an operating room. The method includes, with a computer of a surgical cart disposed within the operating room: determining a network name; determining a password; determining a uniform resource locator; determining a code; providing a network settings user interface showing the network name, the password, the uniform resource locator, and the code; and hosting a first web page at an internet protocol address. The method further includes, with an access point of the surgical cart, providing a wireless network having the network name and being protected using the password. The method further includes, during the surgery and with a first client device disposed within the operating room: connecting to the wireless network using the network name and the password; launching a web browser; and navigating the web browser to the uniform resource locator. The method further includes, with the computer of a surgical cart disposed within an operating room: detecting the navigating the web browser to the uniform resource locator; resolving the uniform resource locator to the internet protocol address at which the first web page is hosted; and providing the first web page to the first client device, wherein the first web page includes a user interface element. The method further includes, with the first client device disposed within the operating room: rendering the provided first web page in the web browser; receiving user input representing the code over the user interface element of the first web page in the web browser; and providing the user input to the computer of the surgical cart. The method further includes, with the computer of the surgical cart: receiving the user input representing the code from the client device; and determining a match between the code with the user input representing the code; and during the surgery and with the computer of the surgical cart: after determining the match between the code and the user input representing the code, providing a first surgical application to a first user via the web browser of the first client device based on interactions from the client device; and providing a second surgical application to a second user via a monitor of the surgical cart.

In an example, there is a system that includes: a surgical cart that includes a local client access point; a primary monitor; and a cart computer. The cart computer includes one or more processors, memory, and a plurality of external interfaces. The plurality of external interfaces include a first external interface coupled to the local client access point; and a second external interface coupled to the primary monitor. The memory comprises instructions that, when executed by the one or more processors, causes the one or more processors to: determine a network name; determine a password; determine a uniform resource locator; determine a code; provide a network settings user interface showing the network name, the password, the uniform resource locator, and the code; host a first web page at an internet protocol address; detect a web browser of a first client device navigating to the uniform resource locator; resolve the uniform resource locator to the internet protocol address at which the first web page is hosted; provide the first web page to the first client device, wherein the first web page includes a user interface element; receive user input representing the code from a client device; determine a match between the code with the user input representing the code; after determining the match between the code and the user input representing the code, provide a first surgical application to a first user via the browser of the first client device based on interactions from the client device; and provide a second surgical application to a second user via the primary monitor of the surgical cart; and wherein the local client access point comprises instructions that, when executed by one or more processors of the local client access point, cause the local client access point to provide a wireless network having the network name and being protected using the password.

DETAILED DESCRIPTION

Disclosed examples include a cart (e.g., referred to as a "technology cart", "surgical cart", or "system cart") for use in an operating room that provides multiple different surgical applications (e.g., navigation, neuromonitoring, surgical planning, imaging, rod bending, and robot control) from the cart. Generally, the cart is a portable unit configured to be readily movable within or between operating rooms usable during an operation to interact with one or more of the multiple surgical applications (e.g., by providing the cart with lockable wheels). In an example, the cart includes a computer, output devices (e.g., a monitor and speaker), input devices (e.g., a touchscreen of the monitor and a keyboard), and connections for other devices (e.g., a network connection, an imaging device connection, and a navigation camera connection). The integration of multiple different applications into the cart can save space in the operating room (e.g., by reducing the need for multiple different stand-alone devices). But the integration of multiple applications into a single cart can cause crowding about the device as users vie for access to the input and output devices of the cart. One way to address the crowding and other challenges is to provide functionality for multiple different client devices (e.g., tablet computers) to interact with functionality provided by the cart from different locations in the operating room. The cart includes networking and server hosting technology to enable multiple client devices to interact with the technology cart in an efficient manner. Further benefits to which implementations can relate include: providing real time instrument navigation and trajectory information to the surgeon during spine surgery, tracking the location of surgical instruments in three dimensional space; locating the anatomical structure in either open or minimally-invasive spinal surgical procedures, minimizing potential of pedicle breach; increasing surgeon efficiency through an expanded offering of software features. An example system in which a cart can operate is described in FIG. 1.

Example System

Figure 1:
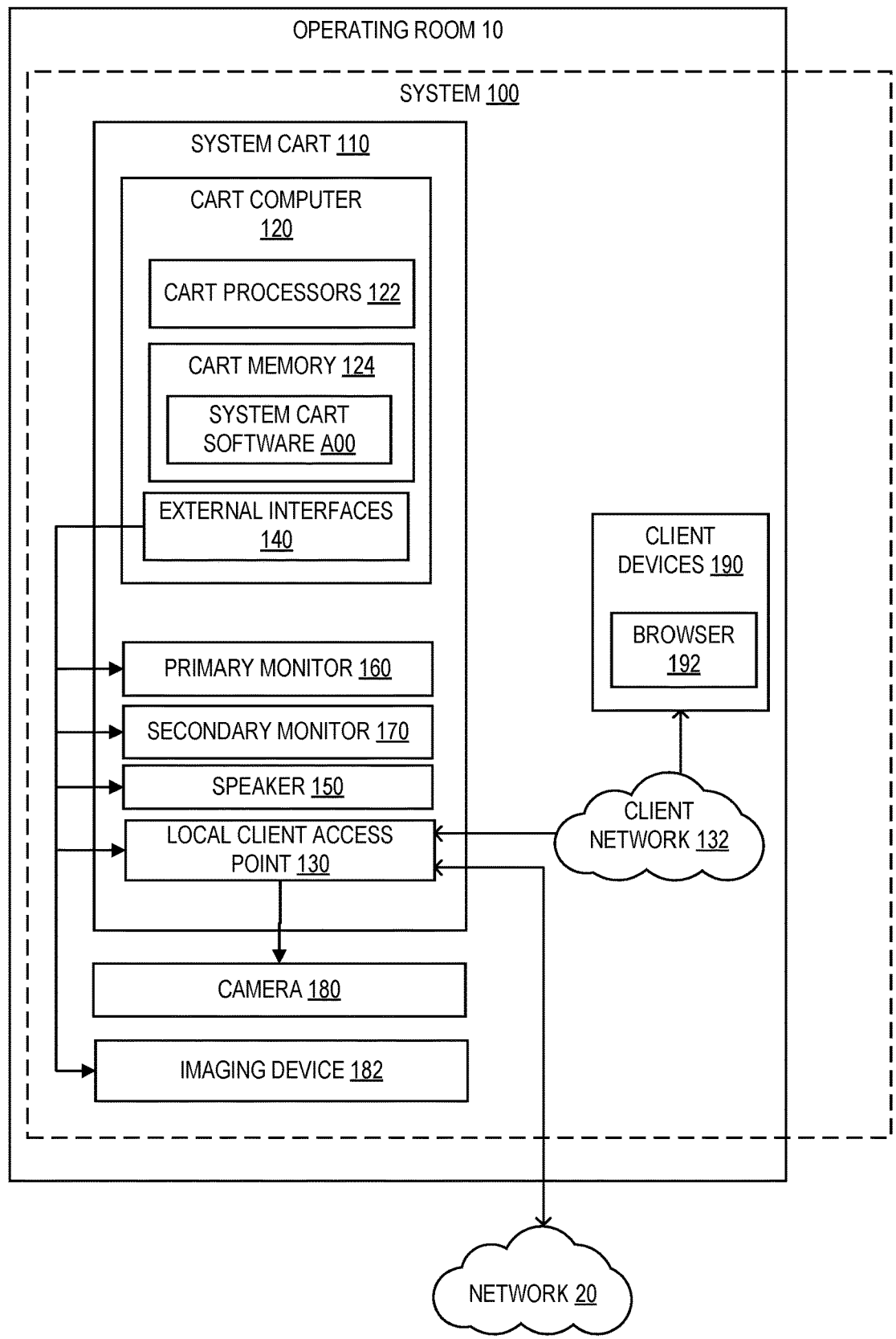
FIG. 1 illustrates an example system having one or more components within an operating room.

FIG. 1 illustrates an example system 100 having one or more components within an operating room 10. The operating room 10 is a room in a hospital, clinic, or other healthcare facility configured for use in a surgery and in which a surgery is routinely performed. The system 100 includes a system cart 110, a camera 180, an imaging device 182, and one or more client devices (e.g., clients) 190. The components of the system 100 can be disposed in the operating room 10 and used from within the operating room 10. The components of the system 100 can be coupled to a network 20. The operating room 10 can include other components for use during the surgery, such as a bed, instrument tray, lights, other technology carts, and other devices and tools. The network 20 can be a set of two or more communicatively coupled computers, such as a local area network, a hospital area network, the Internet, or combinations thereof, among others.

The surgical cart 110 is a mobile station that includes one or more components that provide functions for use during a surgical procedure. For example, as illustrated, the surgical cart 110 includes a cart computer 120, a local client access point 130, a speaker 150, a primary monitor 160, and a secondary monitor 170, among other components.

The cart computer 120 is a computer environment of the cart 110 with which techniques described herein can be implemented. The cart computer 120 is a set of one or more virtual or physical computers configured to cause output based on data (e.g., input). In many examples, the cart computer 120 is a workstation or desktop-style computer but can take other forms. As illustrated, the cart computer 120 includes one or more cart processors 122, cart memory 124, and one or more external interfaces 140.

The one or more cart processors 122 are one or more physical or virtual components configured to obtain (e.g., from the cart memory 123) and execute instructions. In many examples, the one or more cart processors 122 are central processing units, but can take other forms such as microcontrollers, microprocessors, graphics processing units, tensor processing units, other processors, or combinations thereof. In an example, the one or more cart processors 122 include both a central processing unit (e.g., those provided by INTEL or AMD) and a workstation-grade graphics card (e.g., those provided by NVIDIA or AMD).

The cart memory 124 is one or more physical or virtual components configured to store information, such as data or instructions. In some examples, the cart memory 124 includes the computing environment's main memory (e.g., random access memory) or long-term storage memory (e.g., a solid state drive). The memory can be transitory or non-transitory computer-readable or processor-readable storage media.

The external interfaces 140 are a set of one or more components by which the cart computer 120 can provide output or receive input (e.g., from components external to the cart computer 120). For example, the external interfaces 140 can include one or more user input components, such as one or more sensors, buttons, pointers, keyboards, mice, gesture controls, touch controls (e.g., touch-sensitive strips or touch screens), eye trackers, voice recognition controls (e.g., microphones coupled to appropriate natural language processing components), other user input components, or combinations thereof. The external interfaces 140 can include one or more user output components, such as one or more lights, displays, speakers, haptic feedback components, other user output components, or combinations thereof. The interface 1030 can further include one or more components configured to provide output to or receive input from other devices, such as one or more ports (e.g., USB (Universal Serial Bus) ports, THUNDERBOLT ports, serial ports, parallel ports, Ethernet ports) or wireless communication components (e.g., components configured to communicate according to one or more radiofrequency protocols, such as WI-FI, BLUETOOTH, ZIGBEE, or other protocols). In some examples, the interface 1030 includes video input ports to obtain video or image input from devices, such as an intraoperative radiographic imaging device (e.g., a C-arm) or exoscope.

In an example, the external interfaces 140 include: a touch display interface, local client interfaces, camera interface, imaging interfaces, video input, video output, USB interfaces, and remote monitoring interfaces. A USB interface can provide capabilities for USB file system access for exporting log files, screenshots, reports, and diagnostics, as well as importing DICOM (Digital Imaging and Communications in Medicine) data or other data.

In an example, the touch display interface is in the form of a USB port coupled to a touch display (e.g., the primary monitor 160 or the secondary monitor 170). The one or more touch displays coupled to the interfaces can be calibrated for touch using a utility (e.g., "MultiDigimon.exe-touch" as provided with WINDOWS) to select which monitors are included for touch-based input.

The local client interfaces of the external interfaces 140 can include one or more wired and wireless interfaces. In an example, the local client interfaces can include the local client access point 130 (e.g., in the form of a wireless router with an uplink connection to the cart's local wireless control network interface). Wired interfaces can include a dedicated RJ45 network port for connecting a locally wired client. In an example, the wired connection with a client is made first through a wired connection between the cart computer 120 and the local client access point 130 and then between the local client access point 130 and a client device 190.

In an example, the camera interface of the external interfaces 140 is an RJ45 network interface. In some examples, the camera interface provides power to the camera using a power over Ethernet protocol.

In an example, the imaging interfaces of the external interfaces 140 can be network connections for imaging systems, such as those provided by SIEMENS or ZIEHM, among others. The imaging interfaces can be in the form of an RJ45 network interface with static IP addresses. In some examples, the imaging device 182 is connected to the cart computer 120 via sneakernet.

The video input of the external interfaces 140 can include, for example, a DVI-in port or an HDMI-in port connected to a capture card.

The video output of the external interfaces 140 can include, for example, video output for an external monitor. The video output can include, for example, a USB to HDMI adapter for mirroring one of cart's displays to an external HDMI connection. Another example, is a USB to DVI adapter for mirroring one of displays to an external DVI connection.

In an example, the USB ports of the external interfaces 140 can be configured for use in coupling removable drives for use during operation of the cart, such as for exporting reports, logs, or screenshots.

The remote monitoring interface of the external interfaces 140 can include the cart's Internet connectivity that is used to connect the cart 110 to a remote monitoring service for publishing neuromonitoring data for remote oversight.

The local client access point 130 is a networking device configured to communicate with one or more devices through one or more wired or wireless connections. In an example, the local client access point is a special purpose computer configured to manage networking traffic (e.g., receive and transmit data packets according to a networking protocol) among two or more devices coupled to the networking device. The local client access point 130 can be disposed in a dedicated housing separate from a housing of the cart computer 120. In another example, the local client access point 130 can be disposed in a PCIe (Peripheral Component Interconnect Express) card coupled to the cart computer 120. In an example, the local client access point 130 is configured as a special-purpose computing device by executing a networking/firewall operating systems or firmware, such as the open source projects PFSENSE, TOMATO, or DD-WRT or proprietary software. The local client access point 130 can further include special-purpose hardware, such as special-purpose switching hardware.

The local client access point 130 can include one or more antennas and one or more radios configured to provide a wireless client network 132. The antennas, radios, and other components can be configured to provide the wireless client network according to one or more standards such as IEEE 802.11, BLUETOOTH, ZIGBEE, or other protocols. The local client access point 130 can be configured with software to use the one or more antennas or radios to provide the wireless client network 132, such that the one or more client devices 190 can connect thereto.

In some examples, the cart computer 120 communicates directly with the one or more client devices 190 through an ad-hoc connection. The connection can be encrypted or otherwise secured In an example, the cart 110 includes one or more speakers 150. Software running on the cart 110 can provide the ability to generate a sound event based on events detected by the software. The sounds created can be generated by playing an audio file (e.g., a waveform audio file formatted file) using the one or more speakers 150. The tones that can be played and their associated audio files can be defined in each application that provides the ability to play sounds.

The imaging device 182 is a patient imaging device, such as a CT (Computerized Tomography) scanner, an MRI (Magnetic Resonance Imaging) scanner. In an example, the imaging device 182 is in the form of a C-Arm. In an example, the imaging device 182 is in direct communication with the cart 110 (e.g., via a wired or wireless connection) or in indirect communication with the cart 110.

The client devices 190 can be one or more computing devices. Within the context of the system 100, the client devices 190 can be devices used by one or more users during an operation to access services of the cart 110. Advantageously, the client devices 190 can permit multiple users to simultaneously access services provided by the cart 1100 without needing to crowd around the cart. Further, the client devices 190 can be portable computing devices, such as tablets, laptops, phones, wearable devices, virtual reality devices, or augmented reality devices, among others, to enable portable use of the device in a convenient location within the operating room 10. In some examples, the client devices 190 are consumer-grade devices or specialized medical-grade devices. The client devices 190 can include one or more processors, memory, and interface devices (e.g., touch screens), among others. The illustrated client device 190 includes a browser 192. The browser 192 is software that, when executed by the one or more processors of the client device 190, cause the client devices 190 to obtain and render pages, such as web pages (whether or not the web pages themselves are actually obtained from the World Wide Web). Example browsers include CHROMIUM, CRHOME, FIREFOX, SAFARI, INTERNET EXPLORER, EDGE, and OPERA, among others. In an example implementation, the client devices 190 are local client devices in that they are configured to be used within close proximity to the cart 110, such as through use within the operating room 10 by providing features that are relevant to activities happening within the operating room 10. In some examples, the client devices 190 operate as remote terminals that control execution of surgical applications on the cart 110, rather than primarily perform execution of surgical functions on the client device 190.

In some examples, a hardware or software firewall is disposed between the camera and the cart computer 120.

Figure 2:
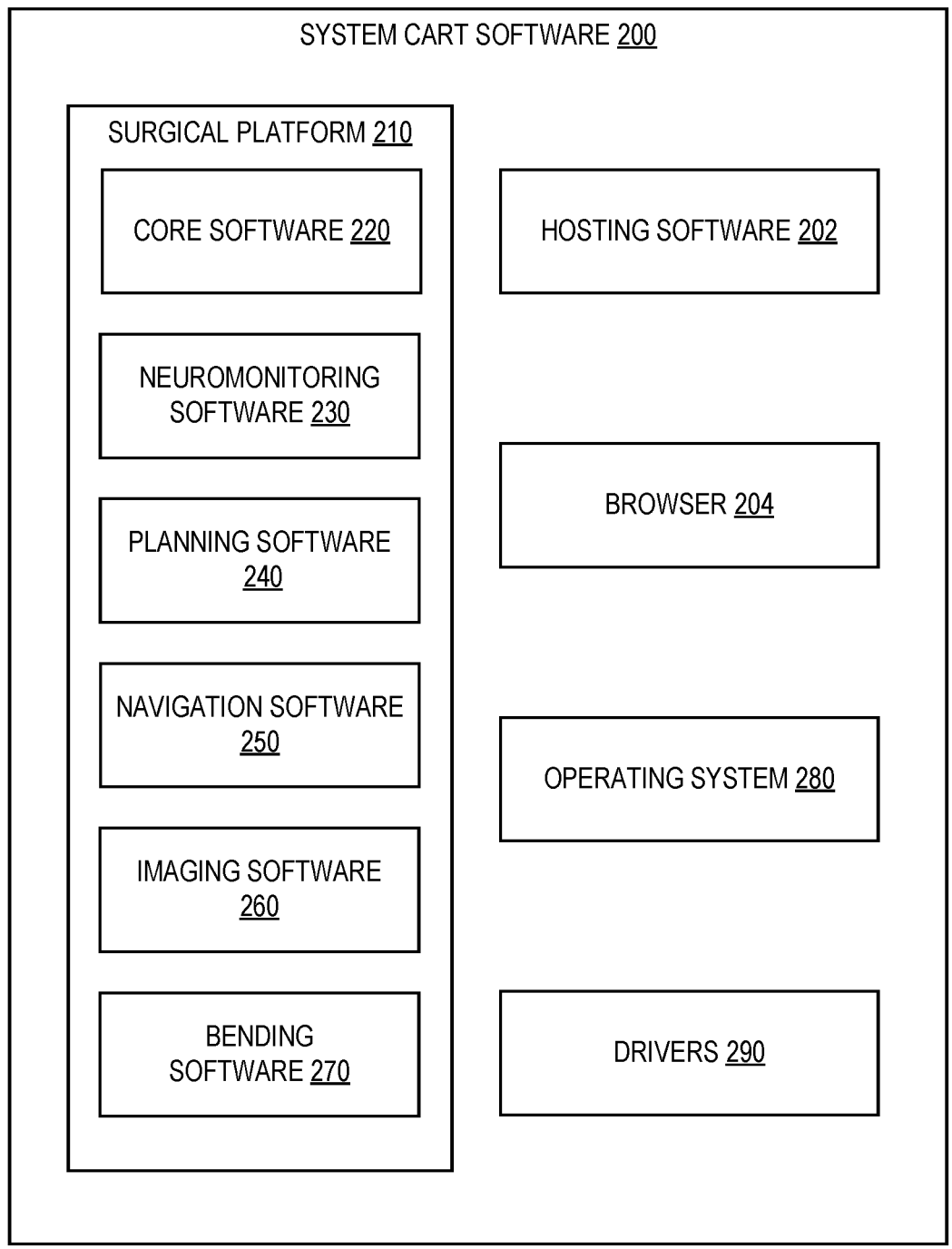
FIG. 2 illustrates system cart software.

FIG. 2 illustrates system cart software 200. The system cart software 200 includes the computer executable instructions and associated components and resources (including, for example, data) to cause one or more processors to perform one or more system cart operations. The system cart software 200 includes hosting software 202, a browser 204, surgical platform software 210, operating system software 280, and drivers 290. The surgical platform software 210 includes core software 220, neuromonitoring software 230, planning software 240, navigation software 250, imaging software 260, and bending software 270.

The hosting software 202 is software that, when executed, causes the cart 110 to provide a web server to which the one or more client devices 190 can connect. In an example, the hosting software is implemented using WINDOWS WEB SEVER (e.g., INTERNET INFORMATION SERVICES by MICROSOFT). While the server may be a web server, the one or more pages or other aspects hosted by the hosting software 202 need not be accessible to devices on the World Wide Web or outside of the operating room 10.

The browser 204 is software that provides a web browser and can include one or more aspects as described above in relation to browser 192. In an example, the browser 204 is an embedded browser or is a headless browser.

The core software 220 includes session management, workflow navigation, network connectivity, image acquisition, camera interface and tracking data, external monitor support, file export (reports, screenshots, logs, images, diagnostics), events and annotation, timers, system maintenance functions. The core software 220 is described in more detail in relation to FIG. 3.

The neuromonitoring software 230 includes the computer executable instructions, associated components, and resources (e.g., data) to cause one or more processors to perform one or more neuromonitoring operations. For example, the neuromonitoring software 230 provides intra-operative neurophysiologic monitoring during spinal surgery. The neuromonitoring software 230 causes the cart 110 to provide information directly to the surgeon, to help assess a patient's neurophysiologic status. The neuromonitoring software 230 can obtain information by causing electrical stimulation of via electrodes located on surgical accessories and monitoring electromyography (EMG), motor evoked potential (MEP), or somatosensory evoked potential (SSEP) responses of nerves. In addition or instead, the neuromonitoring software provides features that permit a surgeon to locate and evaluate nerves for use in nerve avoidance. For instance, the software 230 can provide features for providing proximity information before, during, or after bone preparation and the placement of bone screws. In an example, the neuromonitoring software 230 provides for integrated neuromonitoring. Example neuromonitoring features are described in, for example, U.S. Pat. Nos. 8,538,539; 8,548,579; 8,550,994; 8,556,808; 8,562,521; 8,591,432; 8,602,982; 8,628,469; 8,634,904; 8,663,100; 8,672,840; 8,679,006; 8,696,559; 8,708,899; 8,738,123; 8,747,307; 8,753,271; 8,764,649; 8,768,450; 8,784,330; 8,821,396; 8,942,801; 8,945,004; 8,956,283; 8,977,352; 8,989,866; and 9,037,250, which are hereby incorporated by reference in their entireties for any and all purposes.

The planning software 240 includes the computer executable instructions and associated components and resources (including, for example, data) to cause one or more processors to perform one or more planning operations. Example planning software 240 includes the IGA platform by NUVASIVE, INC. Example planning features are described in, for example, US 2021/0030443, US 2020/0170712, and US 2015/0100091, which are hereby incorporated herein by reference in their entireties for any and all purposes.

The navigation software 250 includes the computer executable instructions and associated components and resources (e.g., data) to cause one or more processors to perform one or more navigation operations. Example navigation features are described in US 2018/0092699, which is hereby incorporated herein by reference in its entirety for any and all purposes.

The imaging software 260 includes the computer executable instructions and associated components and resources (e.g., data) to cause one or more processors to perform one or more imaging operations. Example imaging software 260 includes instructions for obtaining and processing images. Example imaging software 260 includes LESSRAY by NUVASIVE, INC. Example imaging features are described in U.S. Pat. Nos. 8,526,700; 9,510,771; 8,718,346; 8,792,704; 8,908,952; US 2017/0165008; U.S. Pat. Nos. 9,785,246; 10,444,855; and 10,139,920, which are hereby incorporated herein by reference in their entireties for any and all purposes.

The bending software 270 includes the computer executable instructions and associated components and resources (e.g., data) to cause one or more processors to perform one or more bending operations. For example, the bending operations can include planning and providing instructions regarding bending rods for use in a spinal procedure. Example bending software 270 includes BENDINI by NUVASIVE, INC. Example bending software features are described in US 2014/0137618; U.S. Pat. Nos. 9,848,922; 7,957,831; and 8,549,888, which are hereby incorporated herein by reference in their entireties for any and all purposes.

The operating system software 280 includes the computer executable instructions and associated components and resources (e.g., data) to cause one or more processors to perform one or more operations associated with an operating system. The operating system can provide features, such as controlling the allocation of resources (e.g., processing resources, memory resources, and networking resources) and devices (e.g., input devices, output devices, or networking devices) among programs running on a computer. In an example, the operating system software implements an embedded operating system (e.g., WINDOWS IOT by MICROSOFT CORP.) or another kind of operating system (e.g., WINDOWS 11 or WINDOWS 10 ENTERPRISE LTSC by MICROSOFT CORP.).

The drivers 290 include the computer executable instructions and associated components and resources (including, for example, data) to cause one or more processors to perform one or more operations associated with hardware.

The system cart 110 can include other software for use during a medical procedure. In an example, the cart 110 includes software for creating or defining a custom implant for a patient (e.g., a custom interbody implant).

The various software can provide application programming interfaces or other interfaces for communicating among each other. Two or more of the software components can cooperate to perform functions. The software can be configured to perform one or more methods or operations described herein.

The various software can provide user interfaces for providing data to and receiving information from one or more users. Various user interface elements can be used, such as menus, banners, breadcrumbs, buttons, button bars, checkboxes, button lists, toggle buttons, up-down buttons, confirmation dialogs, data pills, date-time elements, drop-down menus, numeric elements, orientation editors, progress bars, scrollable elements, scrollable grids, sliders, spinners, toolbars, tooltips, and wizard steps.

Core Software

Figure 3:
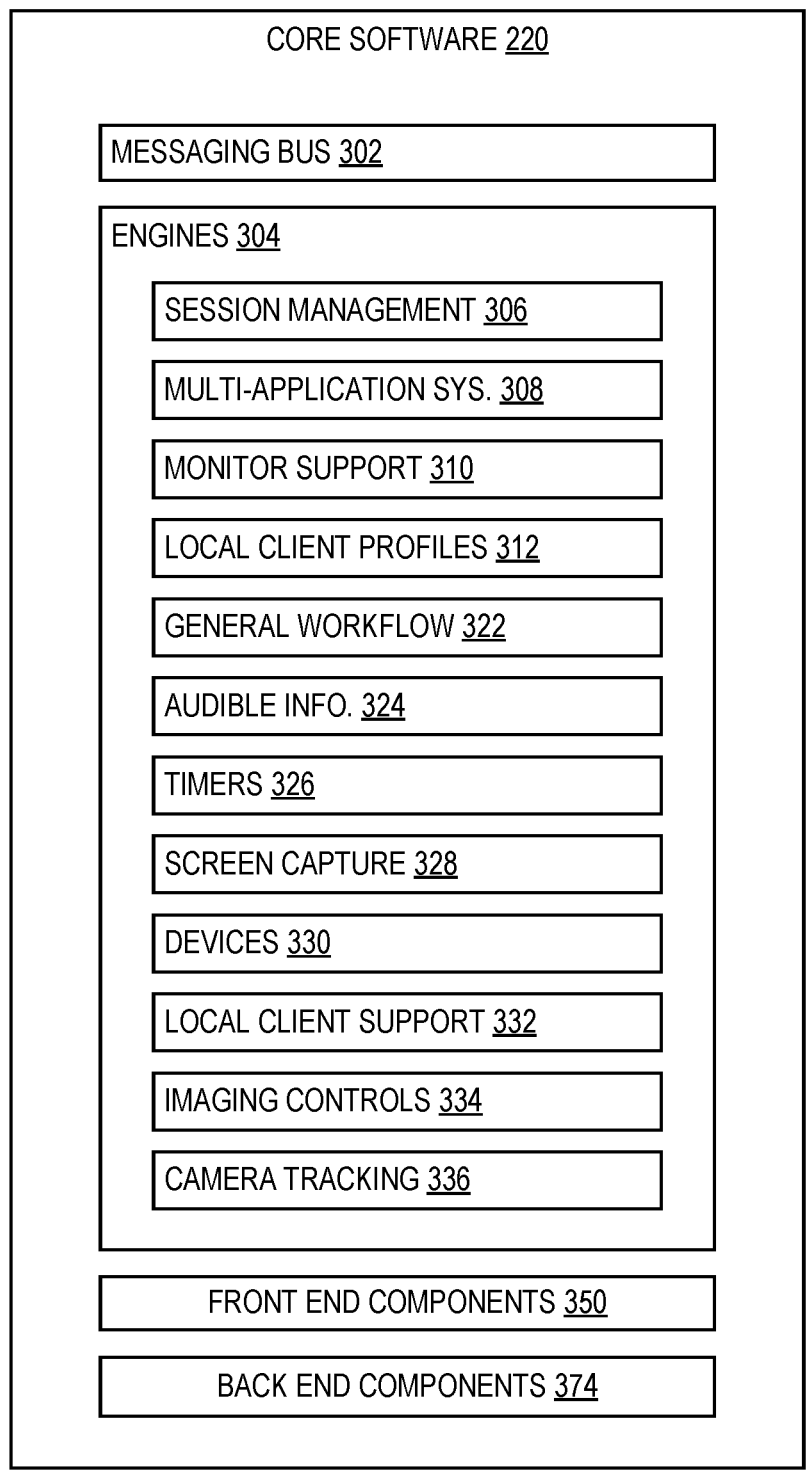
FIG. 3 illustrates core software.

FIG. 3 illustrates the core software 220. Here, "core" means central and does not mean that one or more aspects of the core software are essential to an invention described herein.

As illustrated, the example core software 220 includes engines 304, which can be referred to as sub-units, sub-modules, sub-components, or engines. The decomposition into engines 304 provides modularization of the software and define the scope of functionality that depends on a sub-unit. The core software 220 can be implemented in other ways. In an example implementation, each sub-unit only fulfills its function when incorporated into the core software 220 and, as such, need not be considered to be software unit that can be described or tested in isolation. The modules can be groups of functions and data structures as well as interfaces by which other modules or components can interact with the module. The engines 304 can be software components that include base capabilities from which other applications can be built upon and implements the interfaces to software and hardware components used and shared within each of the supported applications.

The core software 220 can use a message bus 302 with a publish/subscribe design pattern for inter-module and intra-module communication. The message bus can permit decoupling modules as well as de-coupling individual services within a single module. An example implementation supports in-process communication and uses MICROSOFT-.NET events to send messages to subscribers. Bus topics can be configured for each module's configuration file in which the threading and publish/subscribe pattern are specified for each topic of which a module is aware. In some implementations, the core software 220 can be configured such that there are no compile time dependencies between different modules and all interaction between modules is done via the message bus 302 with a publish/subscribe pattern. The bus topics and arguments can be resolved at compile time to ensure type safety during execution. Framework components can be used to define shared topics and argument data types.

As illustrated, the engines 304 include a session management engine 306, a multi-application system engine (e.g., a multi-application system component) 308, a monitor support engine 310, a local client profile (e.g., a local client profile engine) 312, a general workflow engine 322, an audible information engine 324, a timer engine 326, a screen capture engine 328, a devices engine 330, a local client support engine 332, an imaging controls engine 334, a camera tracking engine 336.

The session management engine 306 can provide the ability to start and stop a session within the system 100. A session can correspond to a time period for which the cart 110 is to be used. For instance, a session can correspond to a surgery (e.g., including pre- and post-operative setup and wrap up) for which the cart 110 provides functionality. The current state of the session can be propagated to each connected client device 190 for synchronization. For instance, as the session transitions among start, setup, pre-surgery, intra-operative, and end procedure phases, the current phase can be propagated to each client device 190. In an example implementation, creation of a session includes the creation of a database (e.g., an SQL database) to store session-specific data and a folder or other location to store diagnostic information and screenshots. The session management engine 306 can start or restore a session via request from the user interface elements within a session user interface.

The session management engine 306 can provide functionality for starting a new session, restoring a prior session, and ending a session. Starting a new session can set states to the default initial value for all applications. The session management engine 306 can orchestrate the session start state with each application. Each application can be responsible for performing session startup and notify the core application 220 when the application is ready. Restoring a session can restore all required values. The session management engine 306 can be responsible for notifying each application that a session is being restored with information to identify which session is being restored and notify all applications when a session restore has been completed. Each application can be configured to have the responsibility to perform the restore per application specific session restore requirements. Ending a session prepares the cart 110 for the next new session, such as by notifying applications that a current session has stopped. In response, each application resets its own state as defined in each the application specific software requirement specification. A new database can be prepared for when the next session is started. The session management engine 306 can further orchestrate communication of session state using an event bus including stages for before and after state changes. A component can include base class implementations from which modules derive to encapsulate and simplify session lifecycle management and services without having to individually subscribe to and publish each session lifecycle bus topic.

The multi-application systems component 308 includes software-hardware interfaces for various components, such as external monitor components, imaging components, monitoring accessories, tracking cameras, local client router, hospital network connection, remote monitoring portal, USB interface, and software interfaces, among others. The core multi-application system component 308 can cause the display of device status information related to patient management devices. For example, the component 308 can detect and manage connection state and publish the connection status information and any available version information to the messaging bus 302. The core software 220 can listen on the messaging bus 302 for messages relevant to resource status and propagates the status and any provided version information to the user interface.

In some examples, the core software 220 can provide remote monitoring functionality. The connection to a remote monitoring portal can be provided as part of the core software 220 and use of a network connection to provide access to the Internet and connect to the remote monitoring portal. The ability of the cart 110 to connect to the remote monitoring portal can be managed through the remote monitoring portal by, for example, registering each cart's serial number. A menu item can be provided to start remote monitoring and can be made available when an Internet connection is detected. Once connected to the remote monitoring portal, this menu item becomes chat to invoke a remote monitoring chat dialog.

The multi-application systems engine 308 can interact with stored configuration data. The stored configuration data can include system level configuration values such as: anatomies, approaches, spine levels, workflow definition, session restore options, data retention, file system configuration. The configuration data can include configuration settings for modules with values for: file export, external displays, performance logging, system management operations. There can further be configuration data for imaging devices, such as configuration settings for supported imaging device models. There can be tracking configuration data that can include configuration settings for supported camera. There can be tracking jitter configuration data that includes configuration settings for tracking jitter and noise reduction. There can be log files, such as system log files (e.g., named with the system launch timestamp as part of the file name). Session state data can be stored for session restore and include data regarding enabled applications, selected imaging device model, brightness/contrast, pan/zoom state. In an example, the session state data is stored in a session database or other data stricter. Session data (e.g., data available for export) can include a session data directory containing screen shots and diagnostic files from different applications. An image bank file storage can be a directory of session-specific image bank images mapped to a server file stream.

The monitor support engine 310 facilitates the use of multiple monitors of the cart 110. For example, the example illustrated in FIG. 1 shows the cart 110 having a primary monitor 160 and a second monitor 170. In an example, the monitor support engine 304 causes the primary monitor 160 to display a main screen user interface that includes workflow navigation, setup, pre-surgery, intra-op steps and end procedure capabilities. The secondary monitor 170 can be controlled to display a secondary user interface, such as during an intra-op workflow step. The secondary user interface can include navigation viewports and interface controls.

The monitor support unit can support additional monitors beyond the primary and secondary monitors 160, 170. Such additional monitors can duplicate the contents of the primary or secondary monitors 160, 170 or provide different content. In an example implementation, the interfaces directly supported for the additional monitors are HDMI (High-Definition Multimedia Interface) or DVI (Digital Visual Interface) through ports on the cart 110. If an additional monitor is connected, a resource tile can appear on the primary or secondary monitor 160, 170 with a corresponding label and a settings icon to allow changing which what is displayed on that external monitor.

The local client profiles engine 312 can control the management of one or more aspects of local clients 190. For example, the engine 312 can define at multiple different local client profiles that a user may select from. Example local client profiles include: a neurophysiologist profile, a sales representative profile, and an imaging technician profile. Depending on the profile chosen, the user may be restricted from performing certain functions in the system 100 from the client device 190. In an example, neurophysiologist and company representative (e.g., sales representative) profiles have full access to the functionality of the cart 110 from client devices 190. In an example, the neurophysiologist profile has access to intra-operative monitoring modalities including stimulation. Certain kinds of stimulation, such as motor evoked potential monitoring and trilateral monitoring and assessment programs monitoring can require a remote stimulation setting to be enabled. In an example, the sales representative profile has access to all intra-operative monitoring modalities. For somatosensory evoked potential monitoring, motor evoked potential monitoring and trilateral monitoring and assessment programs monitoring modalities, the sales representative can view the stimulation results and adjust the settings but will not be able to start the stimulation. The cart 110 may cause the client devices 190 to request the neurophysiologist user to confirm they are acting at the request of the surgeon for any changes to electrode settings, stimulation settings and before starting stimulation. In an example, the imaging technician profile is limited to an imaging view and planning functionality with no abilities to perform intra-operative monitoring functionality including changing settings. The imaging technician can be prevented from having access to navigation bending functionality. In an implementation, client profile limitations are set using an authorization claims provider for the specific actions in question. Each application can be responsible for defining each action and assigning the profile for which each action is authorized. These actions can be contained within an authorization model. User interface code can verify the availability of any of these actions using the claims provider interface. An example of permissions and whether they are granted to specific profiles is shown in Table I below:

TABLE 1

|  | Permission for profile: | | |
|---|---|---|---|
| Action | Rep. | Neuro. | Imag. |
| Select Anatomy | Yes | Yes | Yes |
| Select Approach | Yes | Yes | Yes |
| Start Session | Yes | Yes | Yes |
| View Device Connection Status | Yes | Yes | Yes |
| Select Workflow Tabs | Yes | Yes | No |
| Select/Deselect Applications | Yes | Yes | No |
| Read/Write Annotations | Yes | Yes | No |
| Access to reporting | Yes | Yes | No |
| View/Control neuro modality | Yes | Yes | No |
| View/Control planning application | Yes | Yes | No |
| View/Control bending application | Yes | Yes | No |
| View/Control navigation application | Yes | Yes | No |
| View/Control imaging application | Yes | Yes | Yes |

The audible information engine 324 facilitates playing audio. The system 100 can provide a mute/unmute feature and the volume adjustment control such that the system 100 can receive input from users to adjust system volume. The system 100 can provide volume control for the system 100 not only at the cart 110 but also at local client devices 190. Different sounds can have different priorities and different behavior. For example, if sounds are queued up for dynamic stimulation and there is a stimulation error, the stimulation error can interrupt all queued sounds and be played immediately. The audible information engine 324 can be configured such that lower priority sound does not interrupt higher priority sound. The audible information engine 324 can further be configured to set a maximum amount of time that sound is queued before being removed (e.g., sounds waiting in the queue for longer than 500 milliseconds are removed as being stale). In an example, the audible information engine 324 has a rule for audio priority for errors and a further rule that says when sounds of the same priority are playing, errors have the ability to interrupt when sounds of equal or lower priority are playing. Responsive to detecting actuation of the volume adjustment button 504, the system 100 presents the user a system volume control that includes options to mute the entire system 100, as well as a list of modalities with a toggle to turn audio for each modality on and off. If at least one modality is muted, a volume adjustment button can be changed to show sound as muted. If individual applications are muted, and the system volume is muted, un-muting can preserve individually muted application settings. In an example, audio output is monitored to ensure that sound consistently plays through the speaker 150, even if another device (e.g., a client device 190) is connected that can play audio. Example information regarding sound types are shown below in Table II.

TABLE II

| Sound Type | Priority | Loop | Interrupt Rule | Queue On Conflict | Queue Distinct | Queue Timeout (ms) | Play on Dequeue? |
|---|---|---|---|---|---|---|---|
| Start Stim Warning | High | False | Lower Priority | False | N/A | N/A | N/A |
| Stim Response | Medium | If and only if EMG | Equal/Lower Priority | True | True | 1000 | If and only if not looping or if still stimulating |

TABLE II-continued

| Sound Type | Priority | Loop | Interrupt Rule | Queue On Conflict | Queue Distinct | Queue Timeout (ms) | Play on Dequeue? |
|---|---|---|---|---|---|---|---|
| Stim Error | Medium | False | Equal/Lower Priority | True | True | 1000 | Always |
| Free Run Event | Low | False | Lower Priority | True | True | 500 | Always |

The priority property can provide a way of both ranking and grouping sounds. Queued sounds can be played in order of highest priority first. Queued sounds of the same priority are played first-in-first-out. Additionally, the relative priority can be used in determining when to interrupt a sound instead of queuing it using an interrupt rule. The loop can relate to whether to replay the sound indefinitely until pause is called. The interrupt rule can relate to when to interrupt a sound that's already playing. The queue on conflict property can relate to sounds that do not meet the conditions for interrupting another sound and indicates whether to queue the request, otherwise the request can be dropped. The queue distinct property can indicate that only a single request of this audio type should be queued. The queue timeout property can relate to, if the request is queued, how long to allow the request to sit in the queue before playing. The play on dequeue property can relate to, if the request is queued, logic used in a callback to confirm the sound should still be played when finally dequeued. As illustrated above, different sounds types can have different properties, such as priority, loop, interrupt rule, queue on conflict, queue distinct, queue timeout, and play on dequeuer, among others. Priority can be a way of both ranking and grouping sounds. Queued sounds can be played in order of highest priority first. Queued sounds of the same priority can be played according to a first-in-first-out rule. Additionally, the relative priority can be used in determining when to interrupt a sound instead of queuing it using an interrupt rule. Loop can describe whether to replay the sound indefinitely until pause is called. Interrupt rule can specify whether or when to interrupt a sound that is already playing. Queue on conflict can describe whether, if a sound request does not meet the conditions for interrupting another sound, to queue the request or drop the request. The queue distinct property can indicate whether only a single request of this audio type should be queued. The queue timeout property can indicate how long to allow the request to sit in the queue before playing. The play on dequeue property can indicate the logic used in a callback to confirm the sound should still be played when finally dequeued.

The timers engine 326 facilitates the use of timers. Multiple timers can be added to the system 100. The timer action can be available in a system menu button or from a timer button. A timer may be started/resumed, stopped/paused, reset and deleted. The timer can be used to time various aspects of the surgery.

The screen capture engine 328 can be configured to provide the ability of one or more users to capture screen shots (e.g., images or video). In an example, the capturing of screen shots includes capturing one or more screens based on how many screens are being used. For example, if an application that utilizes a secondary monitor 170 is active, then the capture mechanism can capture what is displayed on both the primary and second monitor 160, 170. In some examples, the screen shots are images or video of a subset of a display area. In an example implementation, screen shots are captured using a MICROSOFT DIRECTX graphics interface. In the event this API fails, the system can be configured to revert to using a WINDOWS GDI bit block transfer mechanism to capture the screens. Where the screen shots are images, they can be encoded in the PNG format or other suitable format and saved to the session data folder. In an example, the cart 110 can only capture the screens on the cart 110 itself, rather than what is displayed on client devices 190. If the screen shot action is triggered from a client device 190, the screen shot will capture what is displayed on the cart 110 at the time and not what is on the client device 190. In another example, the screen shot feature can also take screen shots of what is displayed on the client devices 190 but not the cart 110. In yet another example, the screen shot feature captures what is displayed on all client devices and the cart 110.

The device engine 330 can control how multiple devices interact. In an example, the devices are managed by back end components. For example, an imaging device component provides an imaging device resource, an intraoperative monitoring component provides a patient module resource, and a tracking component can provide a camera resource, which can then be consumed by other software (e.g., applications). Shared bus topics can be used to receive system resource information from loaded components. Components can register the resource and then provide updates regarding connection and health status. Configuring individual resource settings can be the responsibility of each component. The cart 110 can communicate the connection and health status of each resource to the user interface. In an example, the device engine 330 can control the information displayed in a device section of a user interface, which is described in more detail in relation to FIG. 5.

The local client support engine 332 is a component that supports client devices 190. The cart 110 includes a local client access point 130 (e.g., router) connected to the cart computer 120 that provides an access point for local clients 190 to connect to the cart 110. The local client access point 130 can be configured to provide either or both of a wired and wireless connection. In an example, the access point 130 includes a hardware router. Access to the cart 110 through the local client access point 130 can be controlled through a connection passcode generated by the system 100 at run time and displayed only on a specific screen. The local client support engine 332 can be configured to, for example, control connections by local clients 190 to the system 100. The cart 110 can include multiple network interfaces (e.g., wired and wireless network interfaces) that can be connected to a hospital or other network to allow the cart 110 and locally connected clients to connect to the Internet. If both connections are established, the cart 110 can be configured to give one precedence (e.g., the wired connection). When the cart 110 is connected to the Internet, the connection can be shared to local clients 190. For example, the connection can be shared using the Internet connection sharing functionality of WINDOWS. In another example, the Internet connection is made through the access point 130 to both the cart computer 120 and the clients 190. In another example, the Internet connection is made from a hospital network to the cart computer 120 to the access point 130 and then to the clients 190. If the Internet connection is changed from wired to wireless or vice-versa, the Internet connection sharing can be updated to use the connection that has Internet connectivity. If both have connectivity, the cart 110 can use the wired (e.g., Ethernet) connection. Additional information regarding the connection and use of local clients 190 is described at FIG. 7.

The imaging control engine 334 can be configured to provide functionality relating to an imaging device 182 coupled to the cart 110 or data (e.g., images) obtained from the imaging device 182. The imaging control engine 334 provides ability to, for example, choose a desired imaging device model from a drop-down list of supported models, show a connected state or disconnected state of the imaging device 182, shows a current live view from the imaging device 182, pan or zoom to adjust the live image, reset the pan and zoom state back to default, provide controls to adjust brightness and contrast settings of the image.

The imaging control engine 334 can, during a pre-operative or intra-operative portion of the workflow, be configured to: control a view imaging tab of the pre-surgery step, control display of the current live view of the imaging with a live indicator, control pan and zoom, reset pan and zoom state, adjust or reset brightness, adjust or reset contrast, save the current image to the image bank, load an existing image from the image bank, present a user of a client device with an acknowledgement confirmation dialog the first time an image is saved to the image bank from each client, and convert the live indicator to a return to live button that unloads the image and returns the view to the current imaging device live view image responsive to an image being loaded from the image bank. In an example, the imaging control engine 334 can, during an intra-operative portion of the workflow, open an alignment measurements screen and switch to dual view (e.g., live and reference). When switching to dual view, the current live image is saved to the image bank and loaded into the reference view. The reference view provides the same pan/zoom, brightness/contrast, reset and image bank access capabilities as the live view. When the imaging device display is in dual view, there is a copy to reference action button that, upon actuation, saves the current live image to the image bank and immediately load it into the reference view.

The imaging control engine 334, during an end procedure portion of the workflow, can provide features to export imaging device images that were saved to the image bank. These images can be set to be retained only until a new session is created or the session is older than twelve hours. The age of the session can be determined by subtracting an internal time stamp of the session with the current time. The internal time stamp can be continually updated (e.g., every 5 minutes) while the session is active.

The camera tracking engine 336 provides functionality relating to tracking and navigation using the camera 180. The camera tracking engine can further provide functionality for setting up and configuring the camera 180. Example functionality and techniques for providing the camera functionality are provided in US 2018/0092699, which was previously incorporated herein by reference.

The core software 220 further includes front end components 350. The front end components 350 can be components configured to provide user interfaces described herein. Example front end components include an imaging device user interface component, a session user interface component, an image bank user interface component, imaging components, web shell components, user interface utility components, and tracking components, among others.

The core software 220 further includes back end components 360. The back end components 360 can be components configured to provide back end functionality. Example back end components 360 include imaging device components, platform components, tracking components, image framework components, tracking components, and networking components, among others.

The core software 220 can further include client-side frameworks and technologies offering a full stack of plug-and-play capabilities for implementing desktop and browser-based applications (e.g., the applications of the surgical platform 210 and applications providing other functionality described herein). The frameworks can provide a desktop web application featuring or using an HTTP server such as NODEJS or KATANA and an embeddable web browser control such as the CHROMIUM EMBEDDED FRAMEWORK or the JAVA/NET CORE web view. The client-side frameworks can extend that concept by adding plug-and-play capabilities to desktop and the web shells for providing apps capable of running both on the desktop and as a web application. One or more components can be implemented using a set of OWIN (Open Web Interface for .NET) components built by MICROSOFT targeting the traditional .NET runtime. KATANA, and by definition OWIN, allow for chaining together middleware (OWIN-compliant modules) into a pipeline thus offering a modular approach to building web server middleware. For instance, the client-side frameworks can use a Katana pipeline featuring modules such as SIGNALR, security, an HTTP server itself. The plug-and-play capabilities can provide a framework allowing runtime assembly of apps from available plugins. An app built atop of a plug-and-play framework can have dozens of plugins, with some offering infrastructure-level functionality and other offering domain-specific functionality. The CHROMIUM EMBEDDED FRAMEWORK is an open source framework for embedding the CHROMIUM browser engine with bindings for different languages, such as C# or JAVA. OWIN is a standard for an interface between .NET web applications and web servers aiming at decoupling the relationship between ASP.NET applications and IIS by defining a standard interface.

The core software 220 can provide web components, which can be encapsulated, reusable and composable widgets for the web, as defined by the W3C Web Components specification. In the context of the core software 220, there can be at least two types of web components, differentiated by their level of re-usability: custom web components and web plugins. The custom web components are generally/universally reusable web components, not bound to a particular product/domain. The web plugins can be custom web components with strong domain/product focus, reusable only within the context of a family of apps. A web shell component can be an empty shell offering bare-bone plug-and-play support for other web components (e.g., web plugins). The web shell can complement a desktop shell component to offer the client framework. User interface components can include a client-side set of controls built on a, for example, JAVA, CSS, HTML (JCH) development stack and a server side set of matching web request handlers built on, for example, a .NET development stack. While client-side components can follow patterns that enforce separation between pure user interface constructs that represent data (HTML and CSS controls) and JAVASCRIPT code for modeling data and behavior, in the context of the overall architecture, this layer can have one or more properties associated with web views in view portion of the model-view-view model paradigm. Logic (e.g., implemented in JAVASCRIPT) can interact with the server hosting software 202 of the cart 110 by, for example, either pulling data by invoking server-side services (e.g., via REST), pushing data to the server via web sockets (e.g., via SIGNALR or other communication methods), and processing events from the server via similar communication methods (e.g., web sockets or SIGNALR). Server-side logic (primarily, web request handlers, and in some instances, application event handlers) can be implemented in a manner similar to a view model in the model-view-viewmodel paradigm. Depending on a specific task at hand, these handlers can either call application layer services directly by retrieving instances of a required service from a service locator or publish and receive messages (e.g., data) via in-process event bus.

Further example techniques for implementing such computer functions include frameworks and technologies provided by or in conjunction with programming languages and associated libraries. For example, languages such as C, C++, C#, PYTHON, JAVA, JAVASCRIPT, RUST, assembly, HASKELL, other languages, or combinations thereof can be used. Such languages can include or be associated with one or more standard libraries or community provided libraries. Such libraries in the hands of someone skilled in the art can facilitate the creation of software based on descriptions herein, including the receiving, processing, providing, and presenting of data. Example libraries for PYTHON and C++ include OPENCV (e.g., which can be used to implement computer vision and image processing techniques), TENSORFLOW (e.g., which can be used to implement machine learning and artificial intelligence techniques), and GTK (e.g., which can be used to implement user interface elements). Further examples include NUMPY for PYTHON (e.g., which can be used to implement data processing techniques). In addition, other software can provide application programming interfaces that can be interacted with to implement one or more aspects described herein. For example, an operating system for the computing environment (e.g., WINDOWS by MICROSOFT CORP., MACOS by APPLE INC., or a LINUX-based operating system such as UBUNTU by CANONICAL LTD.) or another component herein (e.g., an operating system of a robot, such as IIQKA.OS or SUNRISE.OS by KUKA ROBOTICS CORPORATION where the robot is a model of KUKA ROBOTICS CORPORATION) can provide application programming interfaces or libraries to usable to implement aspects described herein. As a further example, a provider of the navigation system, laser console, or another component may not only provide hardware components (e.g., a camera or laser generator), but also software components (e.g., libraries, drivers, or applications) usable to implement features with respect to the components.

Clinical Interface and Workflow

Figure 4:
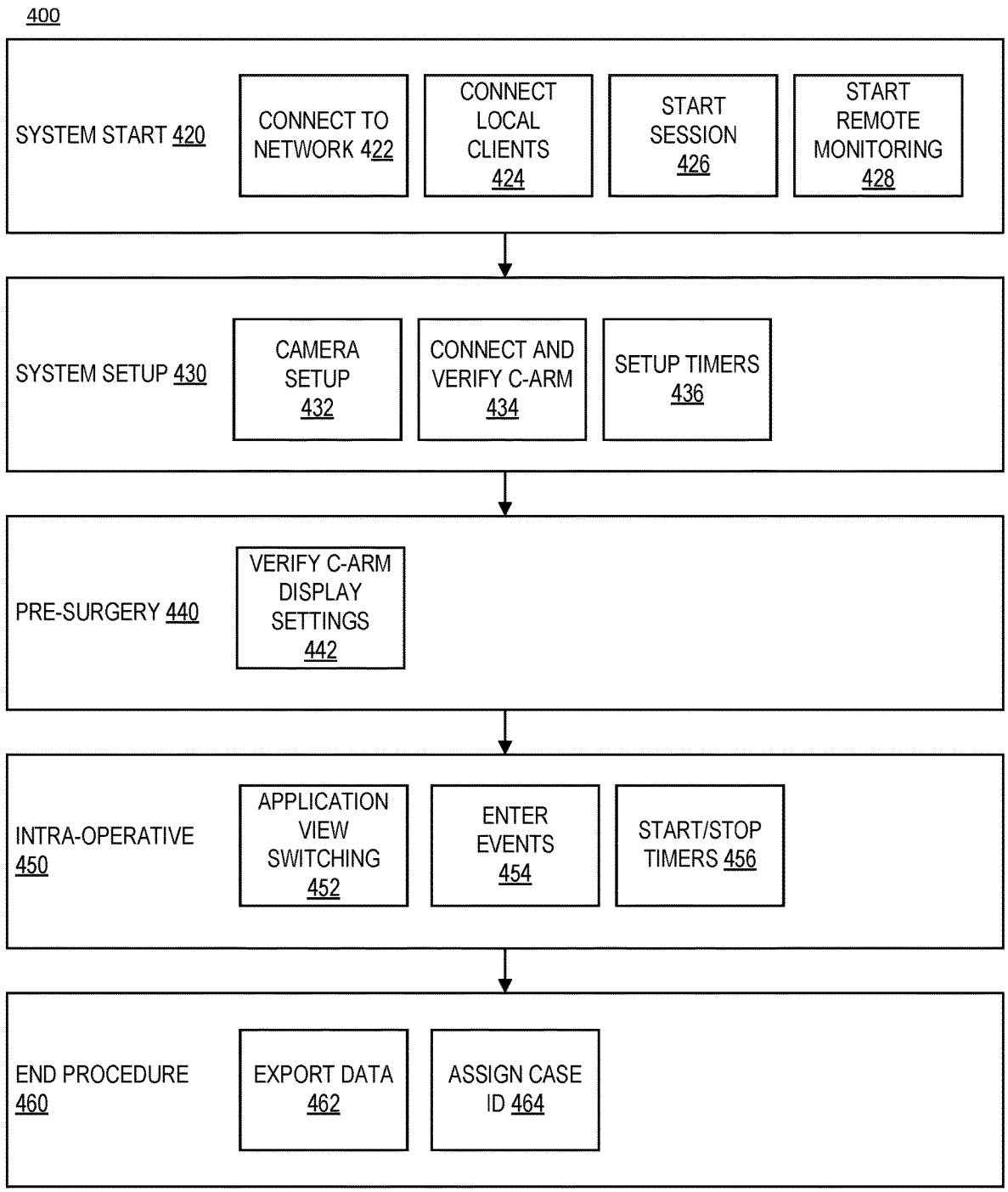
FIG. 4 illustrates a general clinical workflow within which the core software is used.

FIG. 4 illustrates a general clinical workflow 400 within which cart 110 (and the core software 220 thereof) is used. As illustrated, the clinical workflow 400 includes a system start operation 420, a system setup operation 430, a pre-surgery operation 440, an intra-operative operation 450, and an end procedure operation 460.

The system start operation 420 includes one or more operations that prepare the system 100 for use. As illustrated, the system start operation 420 includes a connect to network operation 422, a connect local clients operation 424, a start session operation 426, and a start remote monitoring operation 428.

The connect to network operation 422 includes one or more operations that cause one or more components of the system 100 to obtain access to the network 20. The operation 422 can include, for example, forming a wired connection between a component of the system 100 and a network access point (e.g., connecting to an Ethernet wall jack and an Ethernet port of a component of the system 100 using an Ethernet cable). For instance, the operation 422 can include connecting the cart computer 120 to a local area network provided by a hospital by connecting an Ethernet cable between an external interface 140 of the cart computer 120 and a registered jack network interface (e.g., RJ45) provided within the operating room 10. In another instance, the local client access point 130 is connected to the interface provided within the operating room rather than the cart computer 120. In another example, the operation 422 can include forming a wireless connection, such as by connecting a component of the system 100 to the network 20 using a wireless protocol (e.g., a wireless radiofrequency protocol), such as BLUETOOTH, WIFI, or cellular (e.g., 5G). The operation 422 can further include one or more operations relating to authenticating to the network (e.g., via supplying one or more appropriate credentials, passwords, or user names) and performing networking handshakes.

The connect local clients operation 424 includes one or more operations that cause one or more of the client devices 190 to connect to one or more other components of the system 100 or the network connected in operation 422. An example process for connecting the local client devices 190 is described in more detail in relation to FIG. 7.

The start session operation 426 can include starting a session for use in performing a surgery (or performing training or testing relating to using the system 100 in performing a surgery). The operation 426 can include configuring and launching one or more software components (e.g., software components described above) for use in the surgery. In an example, prior to or during the operation 426, the system 100 receives from a user an indication of the kind of surgery to be performed, the anatomical location on which the surgery will be performed (e.g., cervical anatomy, thoracic anatomy, or lumbar anatomy) and the approach to be used (e.g., anterior, lateral, or posterior).

The start remote monitoring operation 428 can include performing one more operations to enable remote monitoring of one or more components of the system 100. For example, the system 100 can support remote neuromonitoring. During remote neuromonitoring one or more components of the system 100 can provide neuromonitoring data to a remote party and receive data in response. For example, remote monitoring can include NUVAREMOTE as provided by NUVASIVE, INC. In an example, a neuromonitoring local client device 190 that has an Internet connection established through the cart 110 connects to a remote server associated with a remote neuromonitoring service (e.g., NUVAREMOTE by NUVASIVE). As part of the connection, the local client device 190 may obtain from the user and provide to the service credentials or other data used for authenticating the user.

The system setup operation 430 can include one or more operations that setup the system 100 for use in the surgery. In an example, the operation 430 can include providing a startup user interface as shown in FIG. 5.

Figure 5:
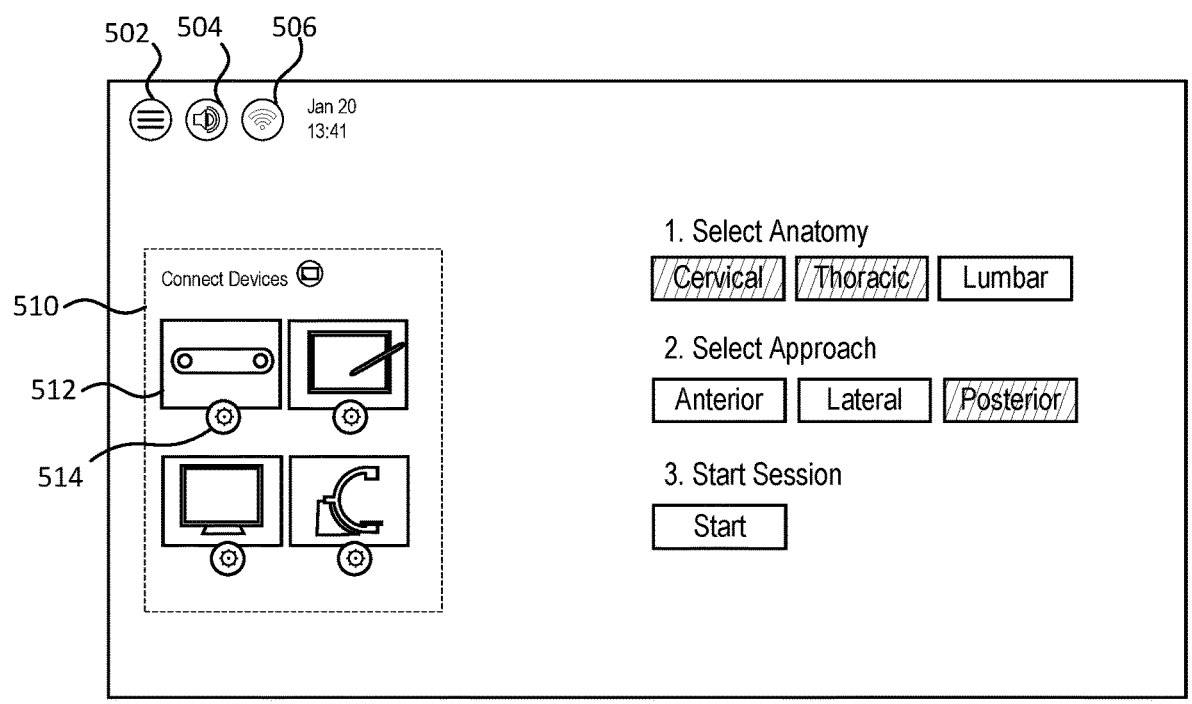
FIG. 5 illustrates an example startup user interface.

FIG. 5 illustrates an example startup user interface 500. The startup user interface 500 can provide the ability for the cart 110 to receive user selection of one or more anatomical regions of the spine and one or more surgical approaches (e.g., anterior, lateral, or posterior spine approaches). The selections available can be defined in a configuration file. The core software 220 can create an intra-operative tab for each approach to help define and control workflow through the various stages of a surgical procedure and provides the anatomical selections to each of the included applications to provide option availability and default settings. The startup user interface 500 includes a menu button 502 actuatable to provide a menu, a volume button 504 actuatable to permit a user to change a volume of the cart 110, and a network button 506 actuatable to permit the user to change network settings of the cart 110. The startup user interface 500 includes a devices section (e.g., a devices region) 510. The devices section 510 provides one or more user actuatable buttons that a user can use to connect and configure one or more devices connected to the cart 110, such as cameras 180, imaging device 182, or client devices 190. In some implementations, the devices section 510 only displays connected remote client devices (which may or may not be configurable from this user interface 500). In an example, connected devices, such as the camera 180 or imaging device 182, are visible or configurable only after starting the session. The startup user interface 500 further illustrates buttons actuatable for a user to select anatomy, to select an approach, and to start a session.

FIG. 5 further illustrates a device region 510 that can be controlled by the device engine 330 to show different devices in separate device icons (e.g., device tiles) 512. The device engine 330 can control the device region 510 and header lines, icons, and labels to, for example, provide a "needs attention" indication (e.g., via color) when additional action is needed and provide an "all set" indicia when no further action is needed. Each different device can be represented by separate device icons 512. In some examples, the device region 510 includes devices that represent additional display interfaces (e.g., laptops, tablets, and monitors) as being separated from the other devices (e.g., neuromonitoring devices or imaging devices) within the device region 510. When a device is disconnected, the background color for that device icon 512 can provide a "needs attention" indicia. In some examples, one or more of the device icons 512 can include a "required" flag depending on the one or more applications selected and the connection status of devices that are depended on. When a connected device has an initialization or communication issues the alert icon can appear on the patient module in the bottom right hand corner. This indicates that a physical connection is complete however there is an error. Pressing on the device with the alert icon can launch a tool tip message box. The tool tip message box can contain text associated with the specific error detected. In some examples, the device region 510 or elsewhere can provide information regarding a connection status between the client devices 190 and the cart 110. For example, device region 510 shows a good wireless signal level indicator (e.g., color coded green) when the roundtrip latency of a signal between the connected devices and the cart 110 is less than 300 milliseconds. The device region 510 shows a caution wireless signal level indicated (e.g., color coded yellow) when the roundtrip latency of a signal between the connected devices and the cart 110 is greater than 300 milliseconds for a period of time less than five seconds. The device region 510 can show a warning wireless signal level indicator (e.g., color coded red) and display a message indicating the client was disconnected from the cart 110 when the roundtrip latency of a signal between the connected devices and the cart 110 is greater than 300 milliseconds for longer than 5 seconds.

FIG. 5 provides an example where one of the icons is a camera, such as an infrared tracking camera for use in navigation, imaging, and bending applications, among others. A camera device icon 512 can be shown in the device region 510 whenever at least one application depending on a camera is enabled (e.g., bending, imaging, or navigation). When the camera is required but unconnected, the camera device icon 512 can provide such an indication (e.g., by being colored red). When the camera is connected and initialized, the tile can change provide such an indication (e.g., by changing from red to gray). When the camera is connected and powered on, an audio tone can be played by the camera and a green LED will light up on the camera. The device icon 512 can include a settings button 514. Upon detecting actuation of the settings button 514, the system 100 can launch a camera setup dialog that provides the ability to switch between a live view (e.g., infrared video from the camera) and an array view (indication of markers visible to the camera). While in camera view there is no tracking data available to applications for markers or rigid bodies. While in array view, the right-side of camera setup can provide an indication of the rigid bodies being tracked and where they appear within the camera's working volume. An example of this is shown in FIG. 6.

Figure 6:
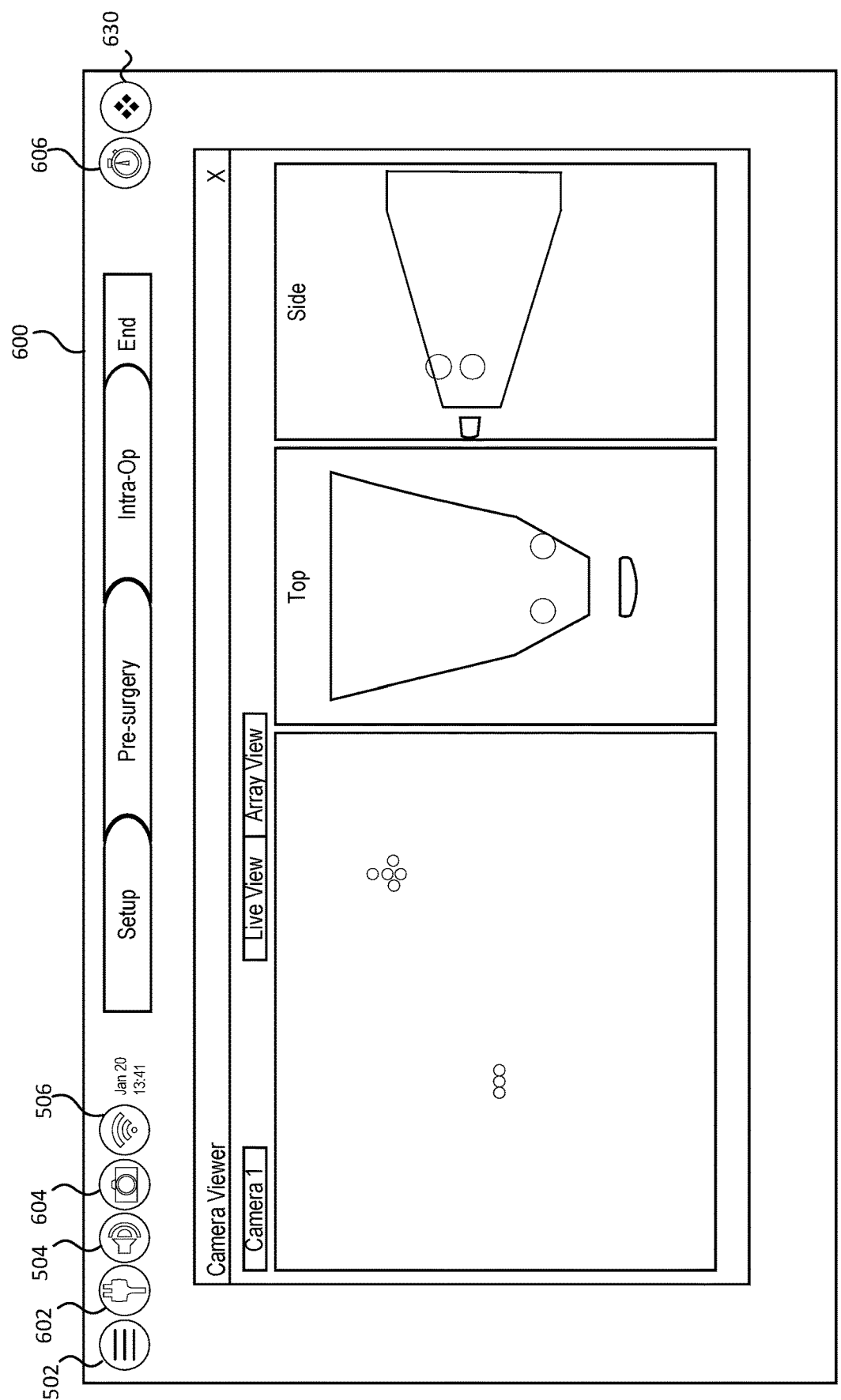
FIG. 6 illustrates a camera setup user interface.

FIG. 6 illustrates a camera setup user interface 600. The user interface 600 includes a menu button 502, a power button 602 actuatable to display power information, a volume button 504, a camera button 604, a network button 506, a timer button 606 actuatable to display a timer menu, and an application button 630. The user interface 600 further includes a camera viewer displaying a representation of one or more markers visible to the camera as well as an estimated representation of the camera's field of view. Such information can facilitate the calibration and setup of the cameras.

Returning to FIG. 5, the device region 510 further shows an imaging device, such as a C-arm. The system 100 can support importing radiographic images from the imaging device 182. In an example implementation, the system 100 can support various different kinds of imaging devices 182. The system 100 can receive from the use a selection of an imaging device type to match the connected imaging device. The selection received from the user can be used to associates specific parameters for importing images from the connected image stream. The images captured can be provided to an imaging device engine or a specific application requesting the image capture. The system 100 can use, for example, an off the shelf frame grabber capture card. The capture card can be connected to the imaging device through, for example, a DVI or HDMI connection. The cart 110 can acquire the images from the imaging device 182 through this connection.

FIG. 5 further shows an external monitor in the device region 510. If an external monitor is connected to the cart 110, a corresponding device tile can appear in the devices region 510. Such a device tile 512 can include a settings button 514 that presents a dialog for controlling which screen is to be duplicated on that connected monitor. In an example, a default setting can be that the secondary screen is duplicated to external displays.

Returning to FIG. 4, as illustrated, the operation 430 can include a camera setup operation 432, an imaging device setup operation 434, and a setup timers operation 436.

The camera setup operation 432 can include connecting and positioning the camera 180. In some examples, during the camera setup operation 432, the cart 110 can provide a user interface configured to facilitate camera setup, such as is shown in FIG. 6.

The imaging device setup operation 434 can include connecting and verifying the imaging device 182. For example, the operation 434 can include connecting the imaging device 182 to one or more of the external interfaces 140 and performing one or more setup operations on the imaging device 182.

The setup timers operation 436 can include performing one or more operations that include initializing one or more timers.

The pre-surgery operation 440 includes performing one or more operations before performing a surgery. As illustrated, the operation 440 can include an imaging device verification operation 442. The imaging device verification operation 442 can include verifying one or more display settings associated with the imaging device 182.

The intra-operative operation 450 includes one or more operations performed during a surgery. As illustrated, the intra-operative operation 450 includes an application view switching operation 452, an enter events operation 454, and a start/stop timers operation 456.

The application view switching operation 452 includes switching among one or more applications provided by the system 100. For example, the operation 452 can include switching among neuromonitoring, planning, navigation, imaging, and bending software responsive to received user input. While providing an application, the application can provide one or more features or functions provided by the application to assist healthcare personnel in performing a surgery. The applications can continue to operate as background applications.

The enter events operation 454 includes receiving and recording one or more surgical events from a user or a component of the system 100. For example, the system 100 can receive, from a user, one or more text annotations (e.g., user-specified text entered in an input field or text generated from a speech to text system based on voice input from a user), one or more selected pre-defined surgical events (e.g., receiving a selection of one or more surgical events from a predetermined list of specific surgical events available from a drop-down menu or other user interface element), or triggered events (e.g., specific events that may be triggered based on activity during the session, such as neurostimulation).

The start/stop timers operation 456 includes starting or stopping one or more timers (e.g., one or more of the timers set up in operation 436). The starting or stopping of timers can be controlled based on user input received at the cart 110 or a client device 190.

The end procedure operation 460 includes performing one or more procedure wrap up operations. As illustrated, the operation 460 includes an export data operation 462 and an assign case identifier operation 464.

The export data operation 462 can include performing one or more operations that export data obtained during the surgery. For example, the data can be a log file and one or more images obtained.

The assign case identifier operation 464 can include assigning a case identifier to the surgery case.

As discussed above, the method 400 can include the system start operation 420, which can include a connect local clients operation 424. That operation 424 is described in more detail in method 700 of FIG. 7.

Client Device Wireless Connection Workflow

Figure 7:
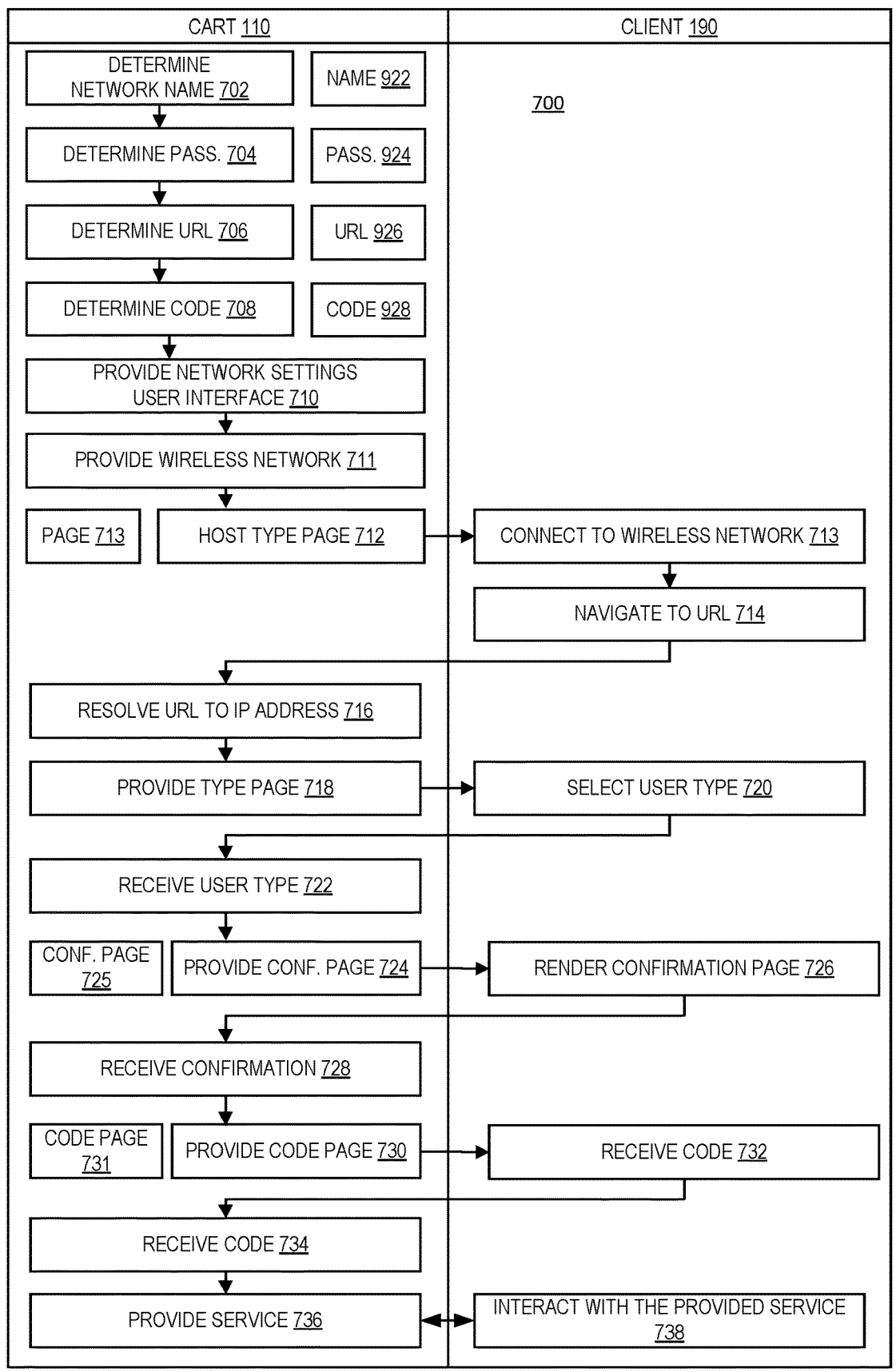
FIG. 7 illustrates an example method for connecting one or more local client devices to the cart.

FIG. 7 illustrates an example method 700 for connecting one or more local client devices 190 to the cart 110, such as may be performed in operation 424 of FIG. 4.

Operation 702 includes to determine a network name 922 for use with the client network 132. The operation 702 can be performed by the cart 110 (e.g., the cart computer 120 thereof). The network name 922 can be the service set identifier (SSID) where the network is created based on the IEEE 802.11 standard. Determining the network name 922 can include loading a predetermined network name 922, receiving a network name 922 specified by a user, receiving a network name 922 specified by the local client access point 103, or obtaining the network name 922 from a network name generator. For example, the network name generator can be an algorithm operating on the cart computer 120 that generates a network name 922 based on one or more criteria. For instance, the algorithm can generate the network name 922 to include certain standard components (e.g., the current date, the name of a current operating room, the name of a hospital, or other components) as well as one or more generated components (e.g., pseudorandomly generated codes of a predetermined fixed or variable length).

Operation 704 includes to determine a password 924. The operation 704 can be performed by the cart 110 (e.g., the cart computer 120 thereof). For example, determining the password 924 can include loading a predetermined password 924, receiving a password 924 specified by a user, receiving a password 924 specified by the local client access point 103, or obtaining the password 924 from a password generator. For example, the password generator can be an algorithm operating on the cart computer 120 that generates a password 924 based on one or more criteria (e.g., length, complexity, or style). For instance, the algorithm can generate the password 924 from pseudorandomly selected letters, numbers, symbols, or words.

Operation 706 includes to determine a URL (Uniform Resource Locator) 926. The operation 706 can be performed by the cart 110 (e.g., the cart computer 120 thereof). For example, determining the URL 926 can include loading a predetermined URL 926, receiving a URL 926 specified by a user, or obtaining the URL 926 from a URL generator. For example, the URL generator can be an algorithm operating on the cart computer 120 that generates a URL based on one or more criteria (e.g., local resource locations).

Operation 708 includes to determine a code 928. The operation 708 can be performed by the cart 110 (e.g., the cart computer 120 thereof). Determining the code 928 can include loading a predetermined code 928, receiving a code 928 specified by a user, or obtaining the code 928 from a code generator. For example, the code generator can be an algorithm operating on the cart computer 120 that generates a code 928 based on one or more criteria (e.g., length, complexity, or style). For instance, the algorithm can generate the code 928 from pseudorandomly selected letters, numbers, symbols, or words. In an example, the code 928 is different from the password. For example, the password 924 is a password for the client network 132 and the code 928 is used for accessing resources provide by the cart 110 after the client device 190 is connected to the wireless client network 132. In an example implementation, local clients 190 with connectivity to the client network 132 are able to connect only after entering a code 928 that is displayed on a monitor of the cart 110 (e.g., the primary monitor 160). The code 928 can be regenerated on every launch of the cart 110 as well as at least once every certain time period (e.g., twenty-four hours) while running. When a user connects from a local wireless client 190, the user may be prompted to provide a user name, which is to be entered with the code and is written to a log file along with a generated unique ID for that user.

Figure 8:
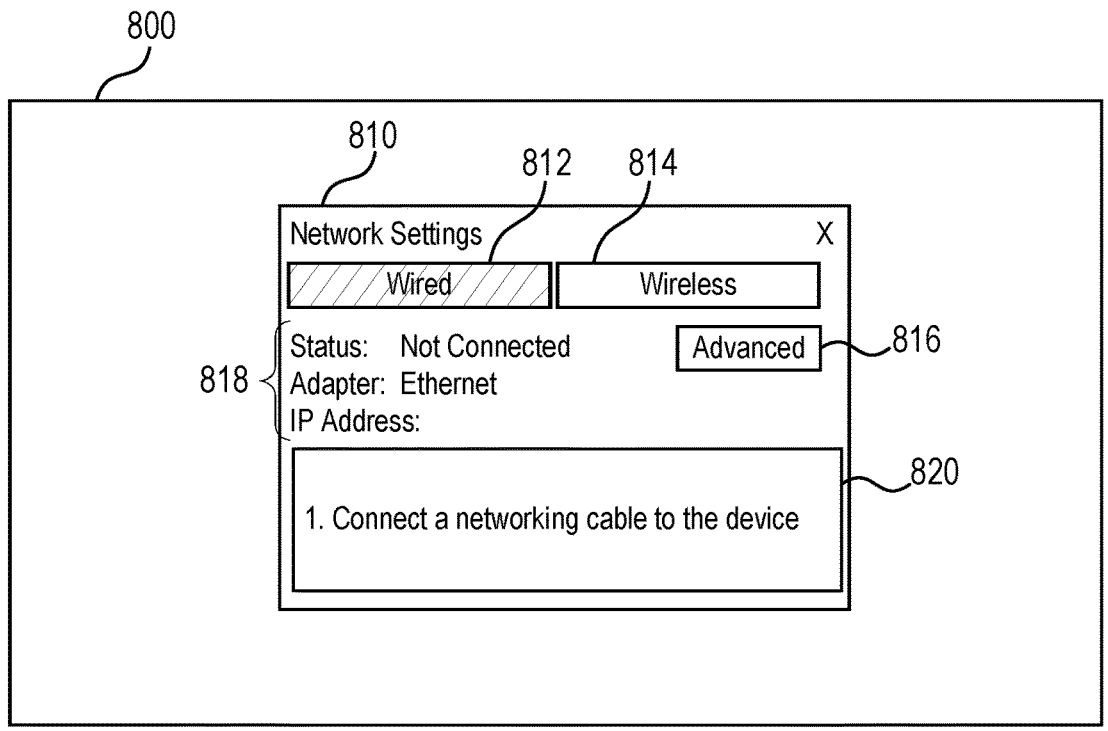
FIG. 8 illustrates an example wired network settings user interface that includes a network settings interface.

Operation 710 includes to provide a network settings user interface 800. The operation 710 can be performed by the cart 110 (e.g., the cart computer 120 thereof). For example, the cart computer 120 can provide the network settings user interface 800 at a display of the cart 110 (e.g., the primary monitor 160). In an example, the cart computer 120 hosts a page having the network settings user interface 800 using the hosting software 202. The cart computer 120 launches the browser 192 by executing browser code and causes the browser 192 to render the network settings user interface 800 by connecting to an address (e.g., as specified by a URL) corresponding to the page being hosted. The network settings user interface 800 is a set of one or more user interfaces that provide network settings information for use by a user in connecting one or more client devices 190. An example wired network settings user interface 800 is shown in FIG. 8. An example wireless network settings interface is shown in FIG. 9.

FIG. 8 illustrates an example wired network settings user interface 800 that includes a network settings interface 810. The network settings interface 810 includes a plurality of connection selectors 812, 814, an advanced selector 816, a status section 818, and an instruction section 820. The connection selectors 812, 814 include a wired connection selector 812 and a wireless connection selector 814. As illustrated the selected wired connection selector 812 indicates that a wired connection has already been selected. The wireless connection selector 814 is a selector that, upon activation, causes the display of the wireless network settings interface 900. The advanced selector 816 is a user-actuatable control that, when activated, causes the display of advanced networking features. The status section 818 indicates the status of various networking aspects, such as a current status (e.g., connected or not connected), a currently used adapter (e.g., Ethernet, WI-FI, or BLUETOOTH), and an IP address. The instruction section 820 provides instructions to the user for how to connect a client device 190. In the illustrated example, the instruction is to connect a networking cable.

Figure 9:
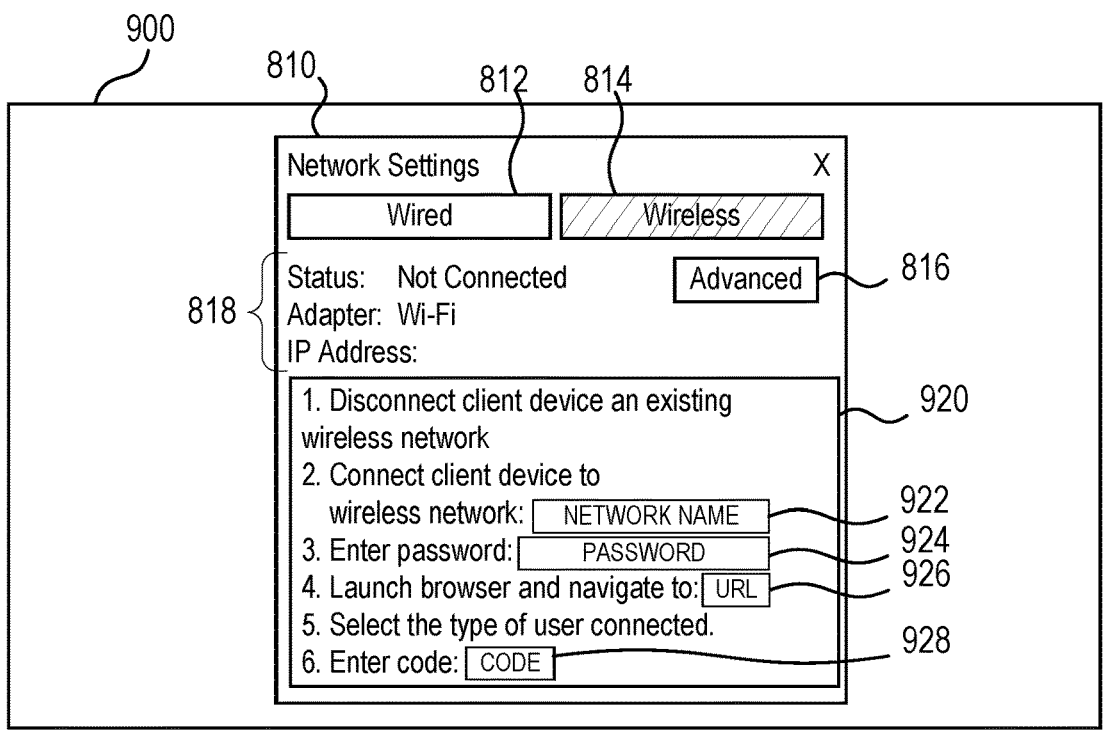
FIG. 9 illustrates an example user interface that includes a network settings interface.

FIG. 9 illustrates an example user interface 800 that includes a network settings interface 810. The network settings interface 810 includes a plurality of connection selectors 812, 814, an advanced selector 816, a status section 818, and an instruction section 820. The connection selectors 812, 814 include a wired connection selector 812 and a wireless connection selector 814. Here, the wireless connection selector 814 indicates that a wireless connection has already been selected. The instruction section 920 illustrates instructions for connecting a client device 190. As illustrated, the instructions include to disconnect the client device 190 from an existing network, connecting the client device to the wireless network having the network name 922, entering the password 924 as the password for the wireless network, navigating to the URL 926 and entering the code 928 on the resulting page. The network name 922, the password 924, the URL 926, and the code 928 can be populated based on the data determined during operations 702, 704, 706, and 708.

Returning to FIG. 7, operation 711 includes to provide a wireless network, such as the client network 132. For example, the client network 132 can be provided using the local client access point 130. The client network 132 can be provided with a name (e.g., SSID) set to the name 922. The client network 132 can support encrypted communications (e.g., using the WPA-2 protocol) using the password 924. In some examples, the providing of the client network 132 can include tuning the power of the wireless network (e.g., which affects the range of the wireless network) to extend to cover the operating room 10 without significant additional coverage beyond the operating room 10. The cart computer 120 can cause the local client access point 130 to provide the client network 132 (e.g., by sending an instruction to the local client access point 130). In another example, the local client access point 130 automatically provides the client network 132 responsive to starting up. The local client access point 130 can include instructions that, when executed by one or more processors of the local client access point 130, cause the local client access point 130 to provide the wireless network. The client network 132 can be provided according to a standard wireless protocol, such as WI-FI, BLUETOOTH, ZIGBEE, or another protocol.

Operation 712 includes to host a type page 713. For example, the cart 110 can host the page 713 at an IP address. The cart 110 can host the page 713 by the cart computer 120 running the hosting software 202 such that the page 713 is provided at the IP address. The page 713 can be a type page 713 that provides one or more selectable user interface elements (e.g., buttons or menus) representing different user types. For example, the user types can be a neurophysiologist type, a representative type, or an imaging technician type, among others. Different client devices 190 can be operated by different users, and the selection of the user type can facilitate customizing the user experience to suit the user. The type can further limit functionality to user types.

Operation 713 includes the client device 190 connecting to the client network 132. For example, the client device 190 receives user input that navigates to a wireless network settings interface of the client device 190 and receives a selection a wireless network having the network name 922. The client device 190 can further receive the password 924 from the user. In some examples, the client device 190 has the network name 922 and password 924 saved and a connection is automatically initiated. The user can obtain the network name 922 and password 924 by looking at a display of the cart computer 120 (e.g., as provided in operation 710) and then manually selecting the network name 922 from among a list of available networks and providing the password 924 at a password prompt. Once the network name 922 and password 924 are available for use for connection, the client device 190 and the local access point 130 can perform a networking handshake and establish a connection between the client device 190 and the local client access point 130. In an alternative implementation, one or more of the password 924 and the network name 922 are provided as part of a machine-readable code (e.g., a QR code) that is displayed by the cart 110. When the client device 190 scans the code, one or more of the steps of connecting to the network 132 can be automated based on information obtained via the code.

Operation 714 includes to navigate to the URL 926. In an example, the URL is received in an address field of a web browser 192 operating on the client device 190 as input from a user. In an example, the browser 192 is a CHROMIUM-based browser. In an example, the operation 714 includes launching the browser 192.

Operation 716 includes for the cart 110 to resolve the URL to the IP address associated with the page. For example, the cart 110 can include its own domain name service that associates the URL with the IP address associated with the page. For example, the cart computer 120 can run a domain name service (e.g., using BIND by ISC). The cart 110 receives the URL 926 navigated to by the web browser 192 over the network 132, and then uses the domain name service to resolve the received URL to the IP address. The IP address can be provided to the client device 190, which the client device (e.g., the browser 192 thereof) accesses to obtain the page 713. In some implementations, the domain name service is configured to redirect traffic from a URL other than the URL 926 to a public DNS (e.g., as provided by GOOGLE, CLOUDFLARE, or OPENDNS), so that navigation to other websites works as expected. For instance, the domain name service can be so configured via one or more configuration files that define one or more URLs and address ranges.

Operation 718 includes to provide the type page 713 to the client device 190. In some examples, the type page 713 is provided over an HTTPS connection. The content of the page 713 provided over the connection between the client device 190 and the cart 110 via the network 132 and can include content provided by the system cart software 200. The hosting software 202 can provide the type page 713 to the client device 190.

Operation 720 includes to receive, at the client device 190 and over the page 713, a user type. For example, the client device 190 receives the page and the browser 192 renders the type page 713 for a user. As described above, the page 713 can include one or more selectable user interface elements (e.g., buttons or menus) representing different user types. The client device 190 can receive a selection of one or more of the different user types. The selection is provided to the cart 110 over the network 132.

Operation 722 includes for the cart 110 to receive the user type. For example, the cart 110 can detect actuation over the connection with the client device 190, such as by receiving a communication from the client device 190 indicating that a particular user type was selected.

Operation 724 includes to provide a confirmation page 725 to the client 190. The confirmation page 725 can be selected or generated based on the received user type. The confirmation page 725 can include a prompt, an affirmative button, and a negative button, among other components. The cart 110 may require selection of the affirmation button before proceeding. In an example, the prompt can vary depending on the user type received in operation 722. Responsive to the user type being a representative or imaging technician, the prompt can indicate that by selecting the affirmative button, the user acknowledges that the user will operate at the direction of a physician. Responsive to the user type being a neurophysiologist, the prompt can ask the user to confirm that they are a trained neurophysiologist with proper credentials to facilitate intraoperative neuromonitoring for the surgical procedure. In some examples, there may be multiple prompts requiring a response prior to continuing. In an example, a prompt asks the user to acknowledge that protected health information is not to be entered or saved into the cart 110. The system can prevent the client device 190 from continuing in the process until the affirmative acknowledgement is made.

Operation 726 includes for the client device 190 to receive the confirmation page 725 from the cart 110. The client device 190 can render the confirmation page 725 within the browser 192. While rendering the confirmation page 725, the client device 190 detects actuation of the affirmative button or the negative button and sends an indication of the actuation to the cart 110.

Operation 728 includes the cart 110 receiving the actuation of the affirmative button or the negative button. Responsive to detecting actuation of the negative button, the cart 110 can provide an error or prevent further access until the affirmative button is actuated. Responsive to receiving an indication of actuation of the affirmative button, the cart 110 can provide a code page to receive a code as described in operation 730.

Operation 730 includes to provide a code page 731 configured to receive a code. For example, the code page 731 can include a text box or other user interface element configured to receive a code from a user and provide the input to the cart 110 for processing. The cart 110 provides the code page 731 to the client device 190 for rendering in the browser 192.

Operation 732 includes for the client device 190 to receive the code page from the cart 110 and render the code page. The client device 190 can receive input from the user of a code. The client device 190 then provides the received code to the cart 110.

Operation 734 includes for the cart 110 to receive the code obtained in operation 732. The received code is then compared to the code 928. Responsive to the codes matching, then cart 110 can proceed to operation 736 where the cart 110 provides services. Responsive to the codes not matching, the cart 110 can cause the client device 190 to display an error indicating that an incorrect code was provided.

In some examples, the cart 110 provides a local client alert message to be displayed at the local client device 190 under specific circumstances and prevent the user from continuing. In an example, the message provided is, responsive to the cart 110 shutting down, a message that the system shut down. In another example, responsive to the number of clients connected to the cart 110 exceeding a predetermined limit of client connections, the cart 110 can provide a message indicating that the number of connected devices has been exceeded and that to connect the client device 190 another connected device should be disconnected first.

Operation 736 includes the cart 110 providing a service. For example, the service can include providing the client device 190 access to features of the surgical platform 210 through the browser 192. For example, the cart 110 can use the hosting software 202 to provide access to the services and applications provided by the surgical platform 210. The same or a different service can be provided to a direct user of the cart 110, such as a user operating an input device of the cart and viewing output of the cart at one or both of the primary monitor 160 and the secondary monitor 170.

In some examples, the cart 110 has a browser 204 that connects to the hosting software 202 the cart 110 uses to provide a server, and a direct user of the cart 110 can access the services through the browser 204 of the cart 110.

In some examples, the method 700 further includes providing Internet (or other network, such as network 20) connection sharing from the cart 110 to the client device 190. For example, the client device can access the Internet via the connection between the device 190 and the cart 110.

Operating 738 includes for the client device 190 to interact with the provided service. For example, during an operating a user can operate the client device 190 to access one or more aspects of the surgical platform 210 to facilitate the surgical operation using the browser 192.

In some examples, the core software application changes all instances of a workflow step (e.g., setup, pre-surgery, intra-operative, or end) on the one or more client devices 190 and the cart 110, when a current workflow step is changed on any client device 190 or the cart 110. The core application can prevent access to another workflow step until an affirmative acknowledgement is received over a user interface.

User Interface

Figure 10:
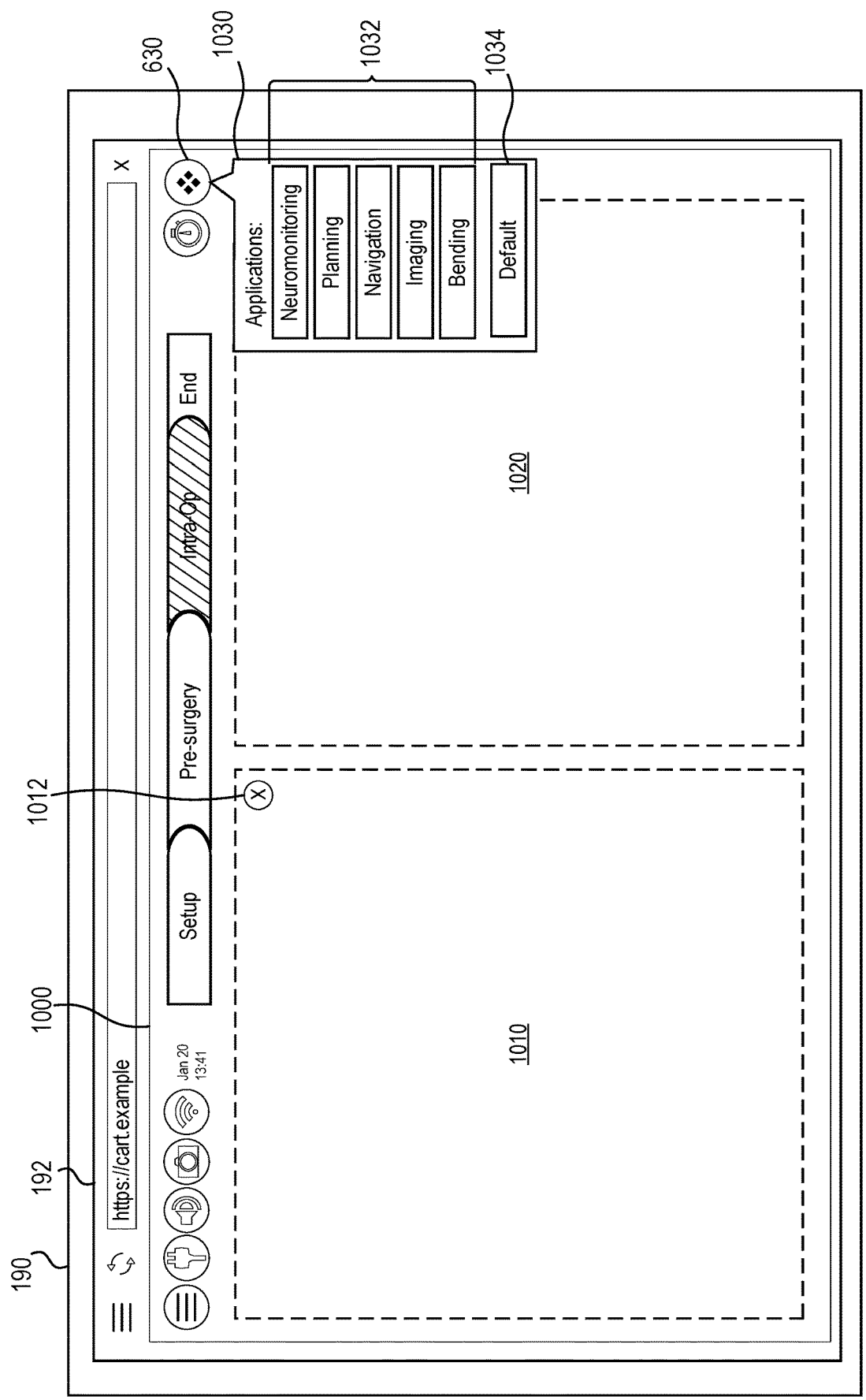
FIG. 10 illustrates an example intra-operative page.

FIG. 10 illustrates an example intra-op page 1000 being rendered in the web browser 192 of the client device 190. Such a page 1000 can also be rendered in the browser 204 of the cart 110. While the web browser 192 is shown as having an address bar and menu, such user interface elements can be hidden (e.g., in a full screen view) so more screen real estate is dedicated to the intra-op page 1000. The intra-op page includes a left panel 1010 and a right panel 1020. The panels 1010, 1020 include a button 1012 that, when actuated, causes the panel 1010, 1020 to close and display a default view. The intra-op page 1000 further includes an application selector 630. The application selector 630, responsive to being actuated by a user, provides a menu 1030 from which the user can select an application to be displayed in the left panel 1010 using one or more buttons 1032, each representing an application to launch. Responsive to a new application being selected, a current view (e.g., in the left or right panels 1010, 1020) is closed and new view corresponding to the new application is provided at the panel.

Among the buttons 1032, is a button 1034 that closes all open application views and displays a default view. For example, the default view can be a view that displays a default imaging view in the left panel 1010 and a neuromonitoring view in the right panel 1020. The button 1034 can be equivalent to closing the existing applications. In some examples, responsive to a user interface element being actuated in the left or right panel 1010, 1020 causes a corresponding view to be opened in the opposite panel 1010, 1020. For example, the right panel 1020 can show a neuromonitoring view with a waveform view button that, when actuated, causes a waveform view to be displayed in the left panel 1010.

Where the intra-op page 1000 is being displayed at a client device 190, there can be a button that causes the client device 190 to show what is being displayed at the cart 110.

In an example, the left panel 1010 has a default view of the imaging device (e.g., a view from a C-arm).

While various descriptions of the aspects of the present disclosure may refer to a surgeon, or surgeons, it is to be understood that the functionality of such aspects may extend to other users, as contextually appropriate, such that the term "surgeon(s)" supports the term "user(s)". In some examples, a surgeon can be a surgical robot.

Examples herein include methods that include operations. Although the operations in each figure are illustrated in a sequential order, the operations may in some instances be performed in parallel, and/or in a different order than those described therein. Also, the various operations may be combined into fewer operations, divided into additional operations, and/or removed based upon the desired implementation.

In addition, diagrams can show the functionality of possible implementations. Operations can represent a module, a segment, or a portion of program code, which includes one or more instructions executable by one or more processors (e.g., CPUs) for implementing specific logical functions or steps in the process. The program code may be stored on any type of computer readable medium, for example, such as a storage device including a disk or hard drive. The computer readable medium may include non-transitory computer-readable media that stores data for short periods of time, such as register memory, processor cache, or Random Access Memory (RAM), and/or persistent long term storage, such as read only memory (ROM), optical or magnetic disks, or compact-disc read only memory (CD-ROM), for example. The computer readable media may be able, or include, any other volatile or non-volatile storage systems. The computer readable medium may be considered a computer readable storage medium, a tangible storage device, or other article of manufacture, for example. The computer-readable medium can be communicatively coupled to the one or more processors. The one or more processors can be coupled to one or more interfaces for providing data to or receiving data from one or more users or other devices. Example interfaces include universal serial busses, displays, speakers, buttons, networking components (e.g., wired or wireless networking components), other interfaces, or combinations thereof).

Operations can represent circuitry that is wired to perform the specific logical functions in the process. Illustrative methods can be carried out in whole in or in part by a component or components in the cloud and in a system. However, it should be understood that the example methods may instead be carried out by other entities or combinations of entities (e.g., by other computing devices and/or combination of computer devices), without departing from the scope of the invention. For example, certain operations can be fully performed by a computing device (or components of a computing device such as one or more processors), or can be distributed across multiple components of the computing device, across multiple computing devices, and/or across a server.

What is claimed is:

1. A method comprising:
 in an operation room and in preparation of or during a surgery:
  receiving, by a cart computer, a network name associated with a network from an access point device;
  receiving, by the cart computer, a password for the network from the access point device;
  receiving, by the cart computer, a uniform resource locator from a user;
  generating, by the cart computer, a code for the network by a code generator algorithm executed by the cart computer based on one or more criteria;
  displaying, by the cart computer, a network settings user interface on a monitor showing the network name, the password, the uniform resource locator, and the code;
  sending, by the cart computer, instructions to the access point device of the cart computer to provide the network;
  hosting, by the cart computer, a first web page at an internet protocol address associated with the uniform resource locator to provide one or more selectable interface elements representing different user types;
  receiving, by the cart computer, a user type selection from a client device from the first web page;
  transmitting, by the cart computer, a confirmation page to the client device based on the user type selection;
  receiving, by the cart computer and from the client device, an actuation of an affirmative button;
  transmitting, by the cart computer, the code to the client device in response to receiving the actuation of the affirmative button;
  receiving, by the cart computer, the code from the client device for accessing resources provided by the cart computer;

comparing, by the cart computer, the received code to the generated code;

in response to determining, by the cart computer, a match between the received code and the generated code during the surgery:

providing, by the cart computer, a first surgical application of a plurality of surgical applications to a first user via a web browser of the client device hosted by the cart computer within the operating room; and providing, by the cart computer, a second surgical application of the plurality of surgical applications to a second user via the monitor of the cart computer.

2. The method of claim 1, further comprising:

sharing, with the client device, an internet connection of the cart computer; and in the operating room, accessing the internet from the client device through the shared connection.

3. The method of claim 2, wherein accessing the internet from the first client device through the shared connection comprises accessing a remote neuromonitoring service via the internet.

4. The method of claim 1, further comprising:

simultaneously hosting, by the cart computer, the first surgical application and the second surgical application with hosting software.

5. The method of claim 1, further comprising:

determining, by the cart computer, a role of the first user of the client device, wherein providing the first surgical application of the plurality of surgical applications to the first user is based on the role, and determining the role of the first user of the client device comprises providing a second page to the web browser, the second page including one or more selectable user interface elements representing different user types and determining actuation of at least one of the one or more selectable user interface elements corresponding to the role.

6. The method of claim 5, wherein the role is selected from the group consisting of: a neurophysiologist, a company representative, and an imaging technician.

7. The method of claim 1, wherein the first surgical application and the second surgical application of the plurality of surgical applications are each selected from the group consisting of: a neuromonitoring application, a planning application, a navigation application, an imaging application, and a rod bending application, wherein the first surgical application is different than the second surgical application.

8. The method of claim 1, wherein providing the second surgical application of the plurality of surgical applications to the second user via the monitor of the cart computer comprises accessing, by the cart computer, the second surgical application with a web browser operating on the computer of the surgical cart.

9. A system comprising:
a surgical cart comprising:
a local client access point;
a primary monitor; and
a cart computer comprising one or more processors, a memory, a first external interface coupled to the local client access point and a second external interface coupled to the primary monitor, wherein the cart computer configured to provide a plurality of surgical applications,
wherein the memory comprises instructions that, when executed by the one or more processors, causes the one or more processors to:

receive a network name associated with a network from the local client access point;

receive a password for the network from the local client access point;

receive a uniform resource locator from a user;

generate a code for the network by a code generator algorithm executed by the cart computer based on one or more criteria;

display a network settings user interface on the primary monitor showing the network name, the password, the uniform resource locator, and the code;

send instructions to the local client access point to provide the network;

host a first web page at an internet protocol address associated with the uniform resource locator to provide one or more selectable interface elements representing different user types;

receive a user type selection from a first client device from the first web page;

transmit a confirmation page to the first client device based on the user type selection;

receive from the first client device an actuation of an affirmative button;

transmit the code to the first client device in response to receiving the actuation of the affirmative button;

receive the code from the first client device for accessing resources provided by the cart computer;

compare the received code to the generated code;

in response to determining a match between the received code and the generated code during a surgery:

provide a first surgical application of the plurality of surgical applications to a first user via a web browser of the first client device hosted by the cart computer within an operating room; and provide a second surgical application of the plurality of surgical applications to a second user via the primary monitor of the surgical cart.

10. The system of claim 9, wherein the memory further comprises instructions that, when executed, cause the one or more processors to:

share, with the first client device, an internet connection of the cart computer.

11. The system of claim 9, wherein the memory further comprises instructions that, when executed, cause the one or more processors to:

determine a role of the first user of the first client device; and wherein provide the first surgical application of the plurality of surgical applications to the first user is based on the role.

12. The system of claim 11, wherein determine the role of the first user of the first client device comprises:

provide a second page to the web browser, the second page including one or more selectable user interface elements representing different user types; and determine actuation of at least one of the one or more selectable user interface elements corresponding to the role.

13. The system of claim 12, wherein the role is selected from the group consisting of a neurophysiologist, a company representative, and an imaging technician.

14. The system of claim 9, wherein the first surgical application and the second surgical application of the plurality of surgical applications are selected from the group consisting of: a neuromonitoring application, a planning application, a navigation application, an imaging application, and a rod bending application, wherein the first surgical application is different than the second surgical application.

15. The system of claim 9, further comprising:
the first client device;
a second client device connected to the local client access point; and
a third client device connected to the local client access point.

16. The system of claim 9, further comprising:
an imaging device; and
a camera.

17. The system of claim 9,
wherein the cart computer is disposed in a cart computer housing; and
wherein the local client access point is disposed in a client access point housing separate from the cart computer housing.

18. The system of claim 17, wherein the local client access point is coupled to the cart computer via an Ethernet cable.

* * * * *